US009522004B2

(12) United States Patent
Demmy

(10) Patent No.: US 9,522,004 B2
(45) Date of Patent: Dec. 20, 2016

(54) DISSECTING TIP FOR SURGICAL STAPLER

(71) Applicant: Covidien LP, Mansfield, MA (US)

(72) Inventor: Todd Demmy, Williamsville, NY (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/269,346

(22) Filed: May 5, 2014

(65) Prior Publication Data

US 2014/0319197 A1      Oct. 30, 2014

Related U.S. Application Data

(63) Continuation of application No. 10/835,543, filed on Apr. 29, 2004, now Pat. No. 8,714,429.

(60) Provisional application No. 60/466,378, filed on Apr. 29, 2003.

(51) Int. Cl.
*A61B 17/068* (2006.01)
*A61B 17/072* (2006.01)
*A61B 17/32* (2006.01)

(52) U.S. Cl.
CPC ......... *A61B 17/0684* (2013.01); *A61B 17/068* (2013.01); *A61B 17/07207* (2013.01); *A61B 2017/07214* (2013.01); *A61B 2017/320044* (2013.01)

(58) Field of Classification Search
CPC ............... A61B 19/34; A61B 2018/00916; A61B 17/122; A61B 17/10; A61B 17/02; A61B 17/064; A61B 17/083; A61B 17/1227; A61L 2202/24

USPC .............. 606/190, 207, 142, 205, 211; 227/175.1–182.1

See application file for complete search history.

(56) References Cited

U.S. PATENT DOCUMENTS

| | | | | |
|---|---|---|---|---|
| 2,887,111 A * | 5/1959 | Leyro Diaz | .......... | A61B 17/282 606/148 |
| 3,575,038 A * | 4/1971 | Mallett | .......... | A61B 17/10 227/19 |
| 3,604,561 A * | 9/1971 | Mallina | .......... | A61B 17/0686 206/339 |
| 3,858,783 A | 1/1975 | Kapitanov et al. | | |
| 4,271,838 A * | 6/1981 | Lasner | .......... | A61B 17/0467 30/124 |
| 4,349,028 A * | 9/1982 | Green | .......... | A61B 17/128 227/175.1 |
| 4,540,110 A * | 9/1985 | Bent et al. | .......... | 227/8 |
| 4,569,346 A * | 2/1986 | Poirier | .......... | A61B 17/122 606/143 |
| 4,574,804 A * | 3/1986 | Kurwa | .......... | A61B 17/282 606/190 |
| 4,576,165 A * | 3/1986 | Green | .......... | A61B 17/128 29/243.56 |
| 4,773,420 A * | 9/1988 | Green | .......... | 227/178.1 |
| 4,872,456 A * | 10/1989 | Hasson | .......... | A61B 17/2812 606/207 |
| 4,935,027 A * | 6/1990 | Yoon | .......... | A61B 17/0469 606/146 |
| 5,014,899 A * | 5/1991 | Presty | .......... | A61B 17/07207 227/151 |
| 5,108,403 A | 4/1992 | Stern | | |
| 5,156,609 A * | 10/1992 | Nakao | .......... | A61B 17/0682 227/179.1 |
| 5,156,633 A | 10/1992 | Smith | | |
| 5,192,288 A * | 3/1993 | Thompson et al. | .......... | 606/143 |

(Continued)

*Primary Examiner* — Robert Long

(57) ABSTRACT

The present disclosure relates to a dissecting tip for use in a surgical stapler or instrument.

23 Claims, 29 Drawing Sheets

(56) References Cited

U.S. PATENT DOCUMENTS

| | | | | |
|---|---|---|---|---|
| 5,193,912 A | * | 3/1993 | Saunders | G01K 1/14 136/232 |
| 5,217,460 A | * | 6/1993 | Knoepfler | A61B 17/29 606/1 |
| 5,219,354 A | | 6/1993 | Choudhury et al. | |
| 5,254,129 A | * | 10/1993 | Alexander | A61B 17/295 30/135 |
| 5,273,519 A | * | 12/1993 | Koros | A61B 17/1611 606/170 |
| 5,282,807 A | | 2/1994 | Knoepfler | |
| 5,304,203 A | * | 4/1994 | El-Mallawany | A61B 17/29 600/564 |
| 5,318,040 A | * | 6/1994 | Kensey et al. | 600/567 |
| 5,322,055 A | * | 6/1994 | Davison | A61B 17/32006 601/2 |
| 5,334,198 A | * | 8/1994 | Hart | A61B 17/0467 606/49 |
| 5,337,937 A | * | 8/1994 | Remiszewski | A61B 17/105 227/182.1 |
| 5,351,871 A | * | 10/1994 | Bauer | A61B 17/0643 227/177.1 |
| 5,376,095 A | * | 12/1994 | Ortiz | A61B 17/0686 227/175.1 |
| 5,389,102 A | * | 2/1995 | Green et al. | 606/143 |
| 5,397,324 A | | 3/1995 | Carroll et al. | |
| 5,403,326 A | * | 4/1995 | Harrison et al. | 606/139 |
| 5,425,745 A | * | 6/1995 | Green et al. | 606/219 |
| 5,476,206 A | * | 12/1995 | Green et al. | 227/176.1 |
| 5,484,095 A | * | 1/1996 | Green | A61B 17/0686 227/175.1 |
| 5,487,500 A | | 1/1996 | Knodel et al. | |
| 5,497,933 A | * | 3/1996 | DeFonzo et al. | 227/175.1 |
| 5,522,788 A | * | 6/1996 | Kuzmak | A61B 17/00234 600/141 |
| 5,586,711 A | | 12/1996 | Plyley et al. | |
| 5,649,957 A | | 7/1997 | Levin | |
| 5,665,100 A | | 9/1997 | Yoon | |
| 5,674,230 A | * | 10/1997 | Tovey | A61B 17/0469 606/139 |
| 5,690,653 A | * | 11/1997 | Richardson | A61B 17/0469 606/148 |
| 5,704,925 A | * | 1/1998 | Otten | A61B 17/00234 604/115 |
| 5,725,532 A | * | 3/1998 | Shoemaker | A61B 17/8866 606/104 |
| 5,749,893 A | | 5/1998 | Vidal et al. | |
| 5,766,187 A | * | 6/1998 | Sugarbaker | 606/148 |
| 5,797,537 A | | 8/1998 | Oberlin et al. | |
| 5,820,009 A | | 10/1998 | Melling et al. | |
| 5,843,099 A | * | 12/1998 | Nichols | A61B 17/0625 606/144 |
| 5,893,855 A | * | 4/1999 | Jacobs | 606/150 |
| 5,922,008 A | * | 7/1999 | Gimpelson | 606/207 |
| 6,001,120 A | | 12/1999 | Levin | |
| 6,004,335 A | | 12/1999 | Vaitekunas et al. | |
| 6,036,714 A | | 3/2000 | Chin | |
| 6,051,006 A | * | 4/2000 | Shluzas | A61B 17/0469 606/144 |
| 6,099,537 A | | 8/2000 | Sugai et al. | |
| 6,205,699 B1 | * | 3/2001 | Bogni | A01K 97/18 43/53.5 |
| 6,206,823 B1 | * | 3/2001 | Kolata | A61B 17/00008 600/127 |
| 6,679,895 B1 | | 1/2004 | Sancoff et al. | |
| 6,755,815 B2 | | 6/2004 | Schultz | |
| 6,761,725 B1 | | 7/2004 | Grayzel et al. | |
| 6,951,568 B1 | * | 10/2005 | Chin | A61B 1/018 600/104 |
| 7,004,950 B1 | * | 2/2006 | Collins et al. | 606/142 |
| 7,208,005 B2 | * | 4/2007 | Frecker | A61B 17/29 606/167 |
| 7,308,998 B2 | | 12/2007 | Mastri et al. | |
| 7,343,920 B2 | * | 3/2008 | Toby | A61B 17/0644 128/898 |
| 7,434,717 B2 | * | 10/2008 | Shelton, IV | A61B 17/07207 227/175.1 |
| 7,452,368 B2 | * | 11/2008 | Liberatore et al. | 606/220 |
| 7,510,106 B2 | * | 3/2009 | Manabe | 227/107 |
| 7,744,613 B2 | * | 6/2010 | Ewers et al. | 606/153 |
| 7,776,057 B2 | * | 8/2010 | Laufer et al. | 606/139 |
| 7,914,543 B2 | * | 3/2011 | Roth et al. | 606/153 |
| 7,997,468 B2 | * | 8/2011 | Farascioni | 227/176.1 |
| 8,091,756 B2 | * | 1/2012 | Viola | 227/178.1 |
| 8,092,378 B2 | * | 1/2012 | Roth | A61B 17/0218 600/206 |
| 8,397,972 B2 | * | 3/2013 | Kostrzewski | A61B 17/07207 227/175.2 |
| 8,496,153 B2 | * | 7/2013 | Demmy | A61B 17/07207 227/175.1 |
| 9,107,662 B2 | * | 8/2015 | Kostrzewski | A61B 17/068 |
| 2001/0034535 A1 | | 10/2001 | Schultz | |
| 2001/0044635 A1 | * | 11/2001 | Niizeki | A61B 10/06 606/205 |
| 2002/0049472 A1 | * | 4/2002 | Coleman et al. | 606/219 |
| 2002/0065534 A1 | * | 5/2002 | Hermann | A61B 17/0643 606/205 |
| 2002/0099368 A1 | * | 7/2002 | Schulze | 606/45 |
| 2002/0099375 A1 | * | 7/2002 | Hess et al. | 606/51 |
| 2002/0183734 A1 | * | 12/2002 | Bommannan | A61B 18/1445 606/32 |
| 2003/0065351 A1 | | 4/2003 | Hess et al. | |
| 2004/0019355 A1 | | 1/2004 | Mehdizadeh | |
| 2004/0193186 A1 | * | 9/2004 | Kortenbach | A61B 17/1285 606/142 |
| 2004/0243151 A1 | * | 12/2004 | Demmy et al. | 606/139 |
| 2005/0080434 A1 | * | 4/2005 | Chung et al. | 606/148 |
| 2005/0113847 A1 | * | 5/2005 | Gadberry | A61B 17/128 606/143 |
| 2007/0282356 A1 | * | 12/2007 | Sonnenschein et al. | 606/153 |
| 2008/0000941 A1 | * | 1/2008 | Sonnenschein et al. | 227/120 |
| 2008/0237297 A1 | * | 10/2008 | Demmy | A61B 17/07207 227/176.1 |
| 2008/0249565 A1 | * | 10/2008 | Michler et al. | 606/219 |
| 2009/0069806 A1 | * | 3/2009 | De La Mora Levy et al. | 606/46 |
| 2010/0094315 A1 | * | 4/2010 | Beardsley et al. | 606/143 |
| 2010/0327042 A1 | * | 12/2010 | Amid et al. | 227/176.1 |
| 2011/0049213 A1 | * | 3/2011 | Schneider et al. | 227/120 |
| 2013/0256378 A1 | * | 10/2013 | Schmid | A61L 31/00 227/176.1 |
| 2013/0256383 A1 | * | 10/2013 | Aronhalt et al. | 227/180.1 |
| 2013/0306704 A1 | * | 11/2013 | Balbierz et al. | 227/176.1 |
| 2013/0334280 A1 | * | 12/2013 | Krehel | A61B 17/07207 227/176.1 |

\* cited by examiner

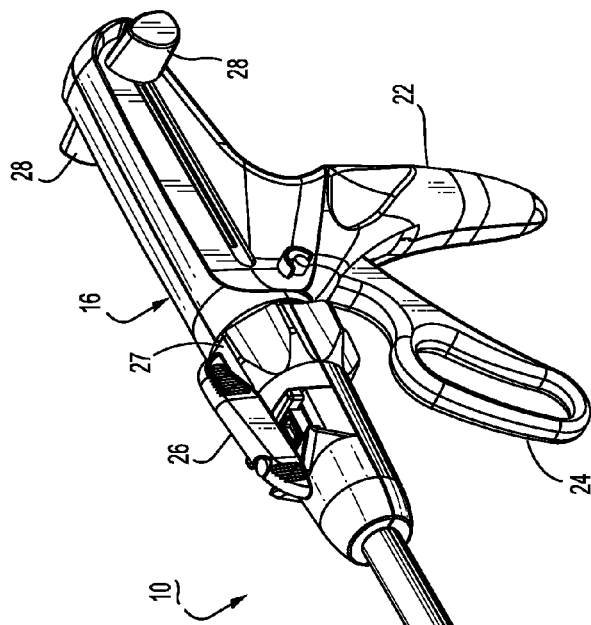
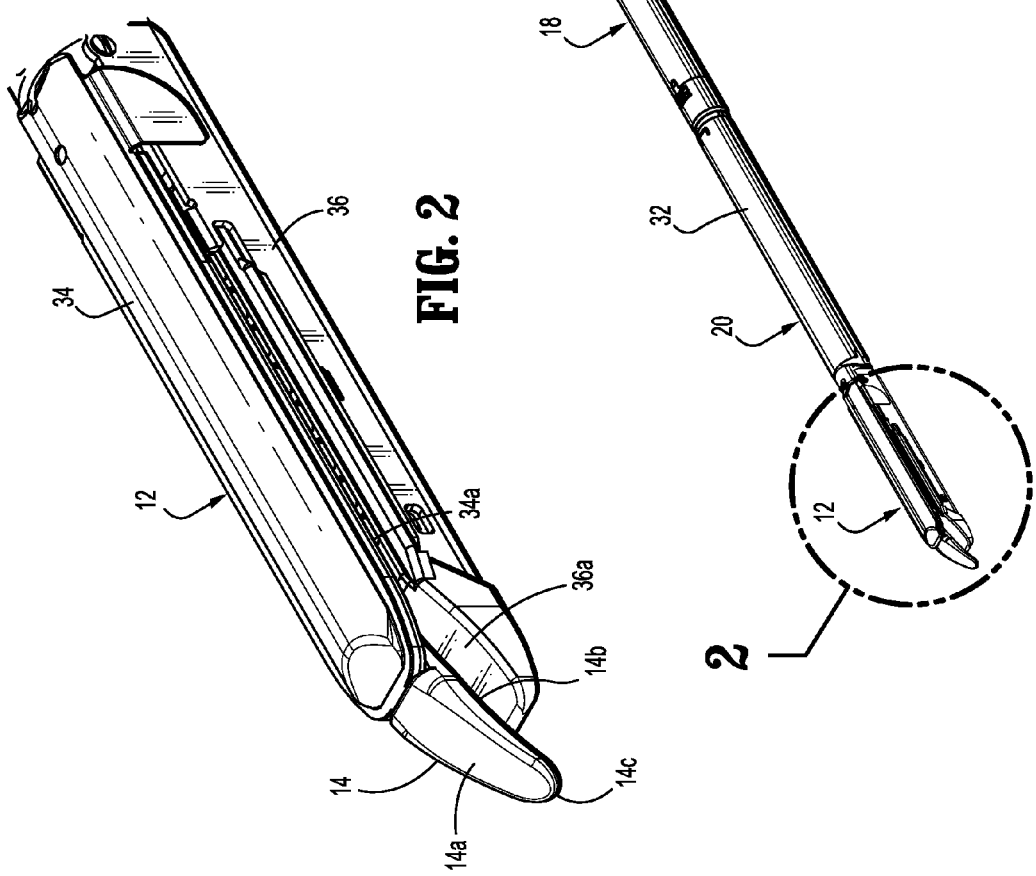

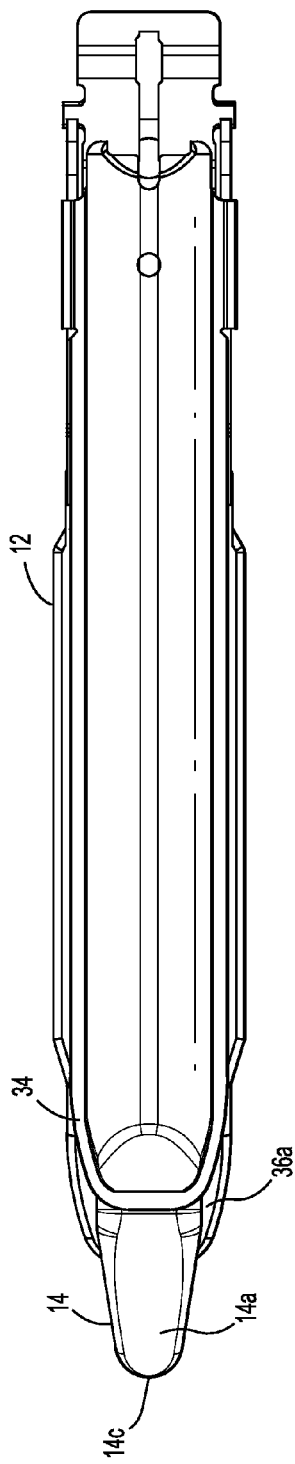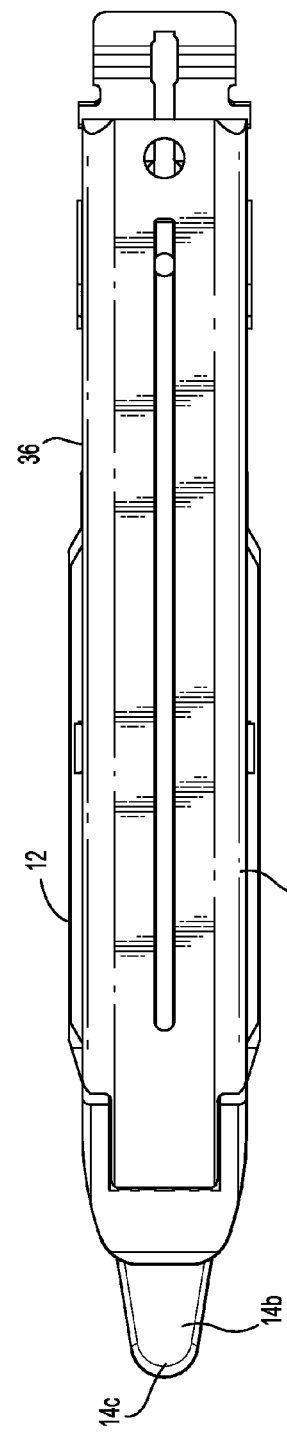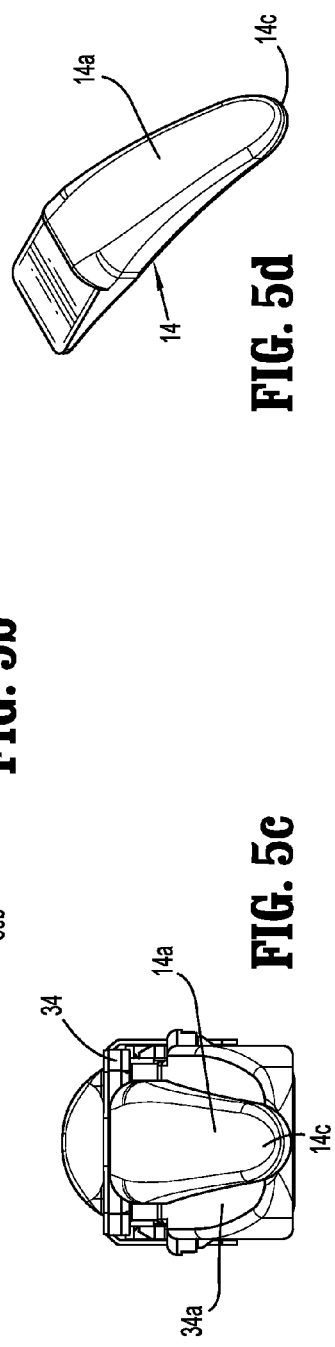

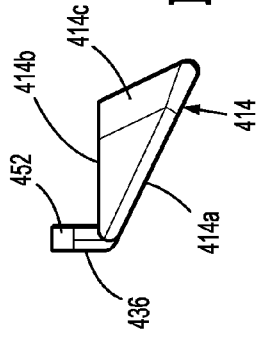
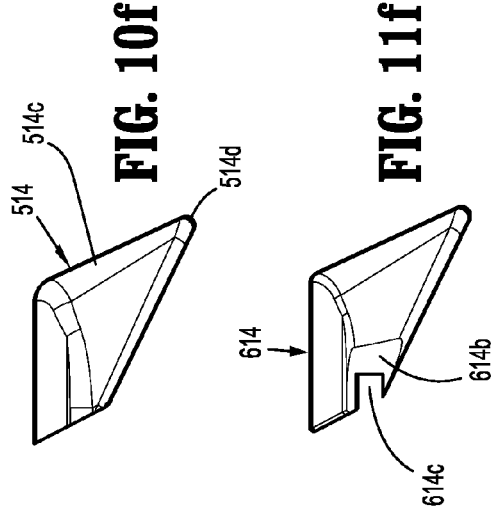
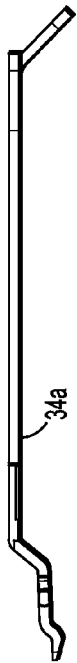
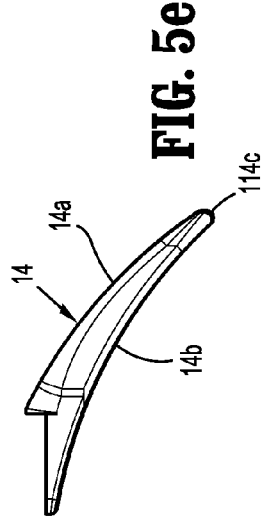
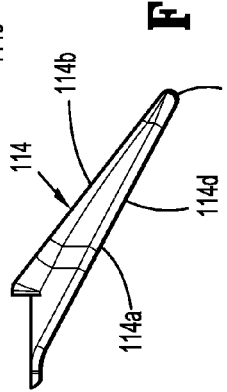
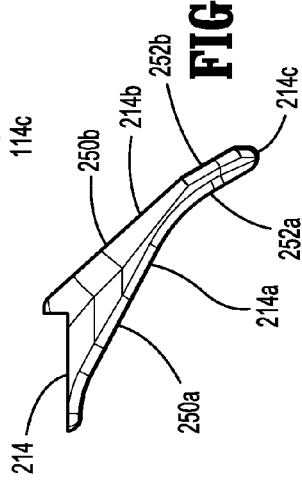
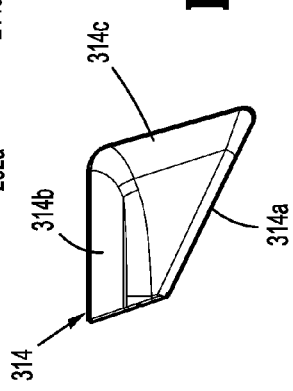

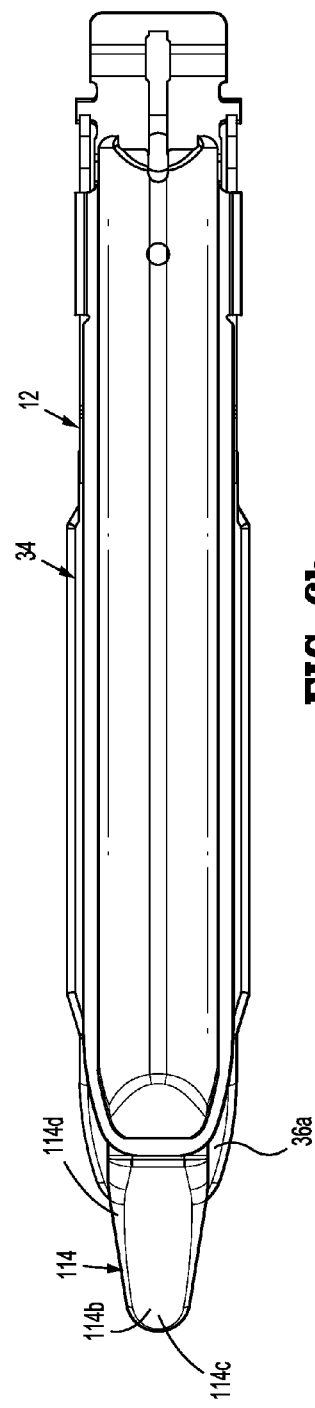
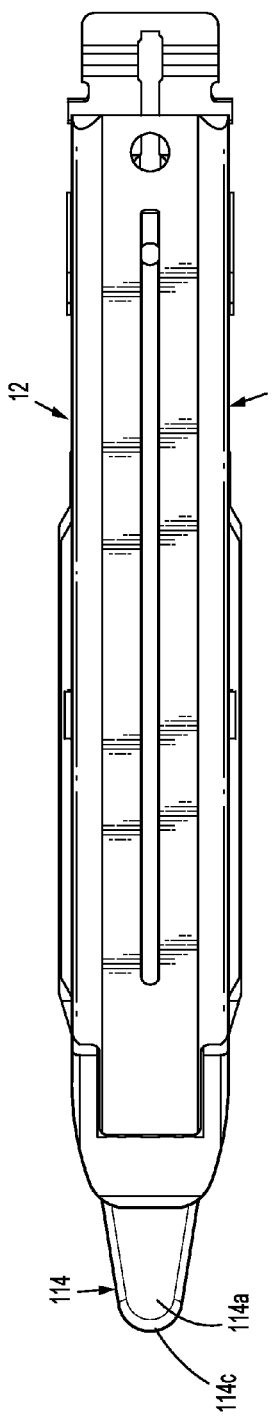
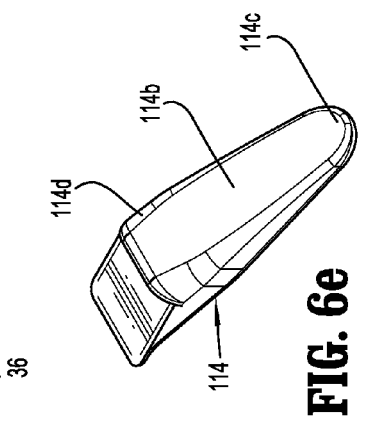
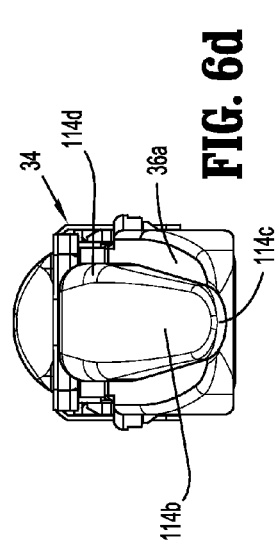
FIG. 6b
FIG. 6c
FIG. 6e
FIG. 6d

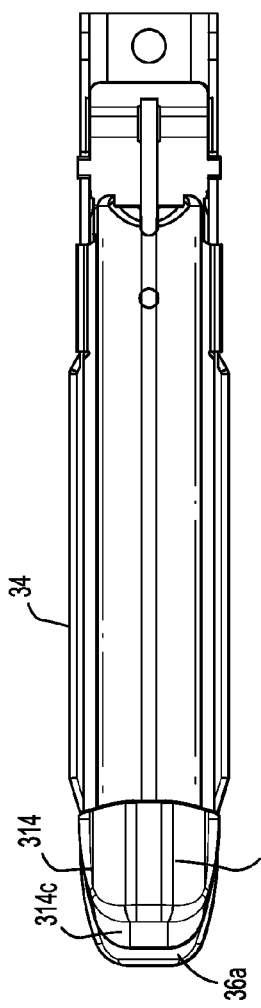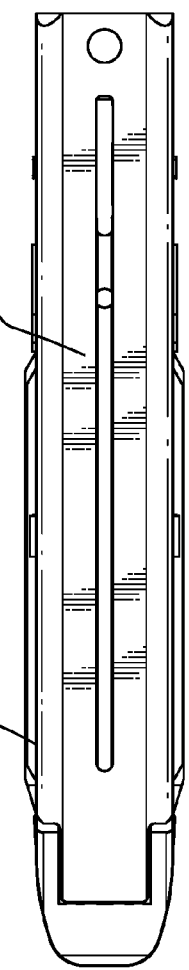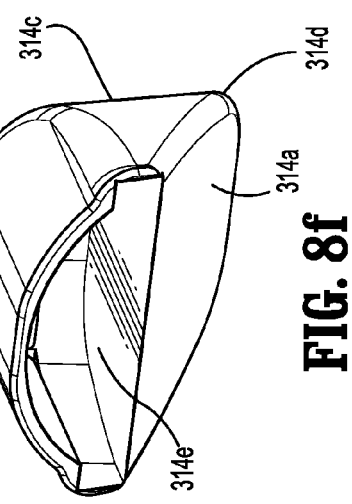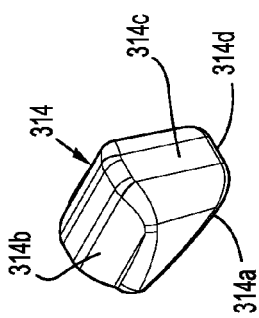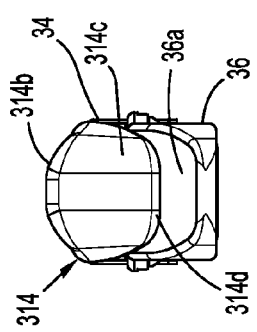

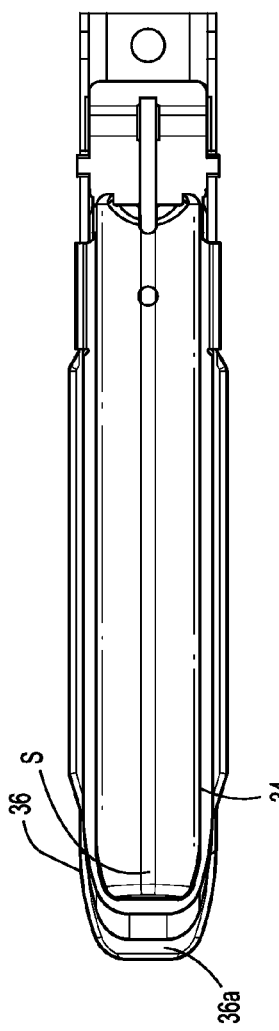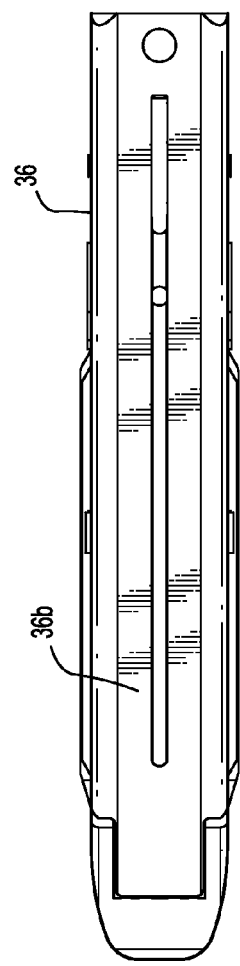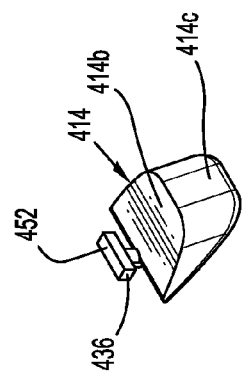
FIG. 9b
FIG. 9c
FIG. 9d
FIG. 9e

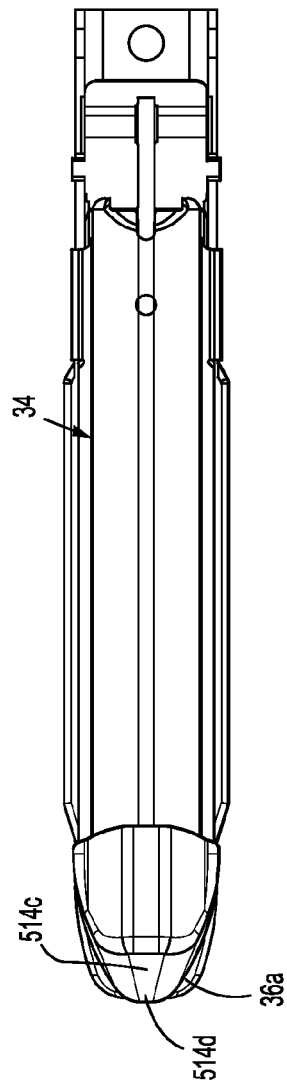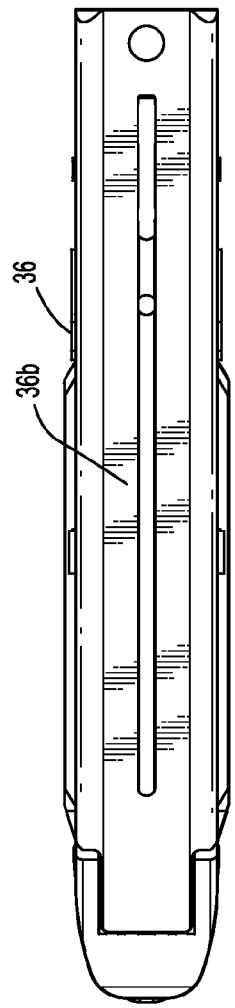
FIG. 10b
FIG. 10c
FIG. 10d
FIG. 10e

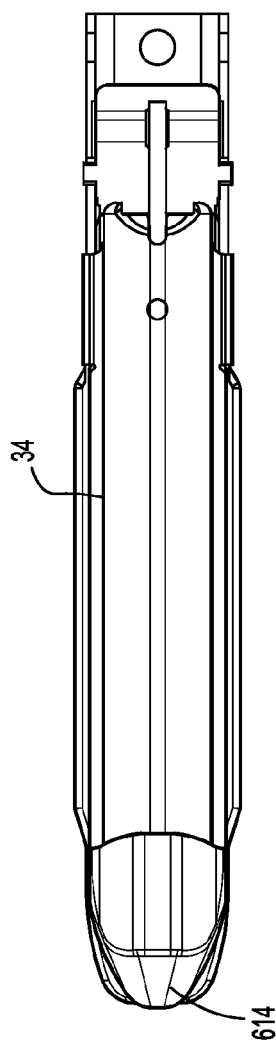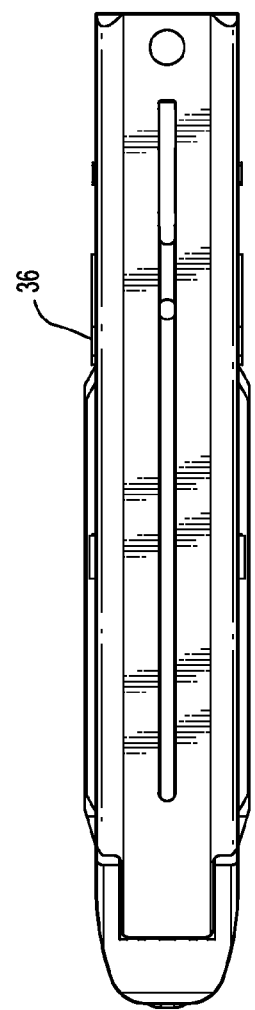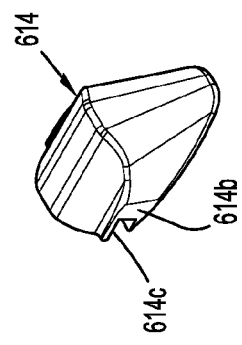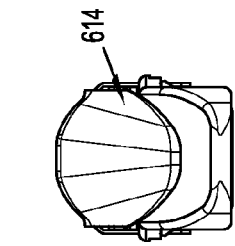
FIG. 11b
FIG. 11c
FIG. 11d
FIG. 11e

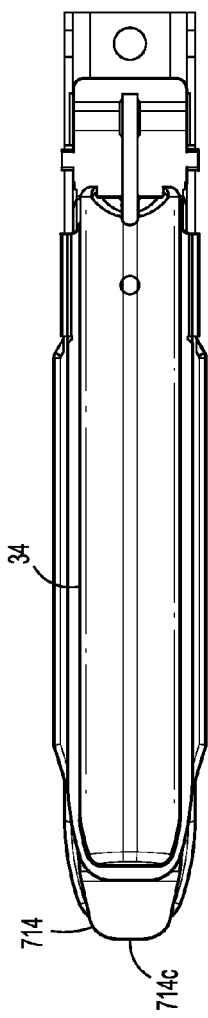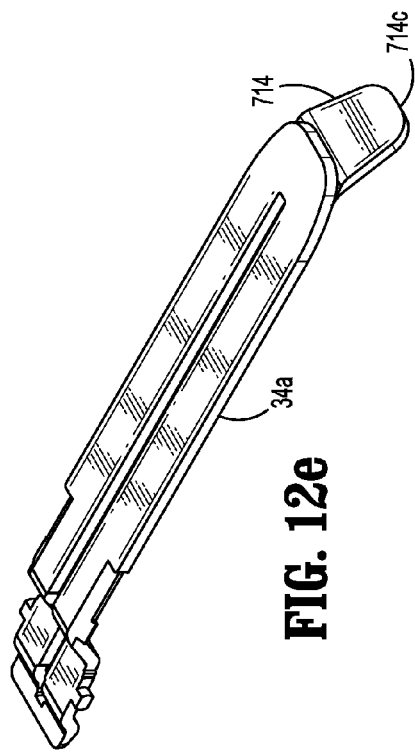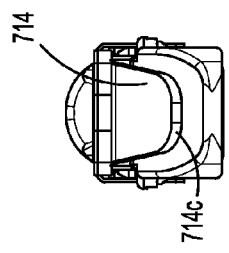
FIG. 12b
FIG. 12c
FIG. 12e
FIG. 12d

DISSECTING TIP FOR SURGICAL STAPLER

CROSS-REFERENCE TO RELATED APPLICATIONS

The present application is a continuation of U.S. patent application Ser. No. 10/835,543 filed Apr. 29, 2004, which claims benefit and priority to U.S. Provisional Patent Application Ser. No. 60/466,378 filed Apr. 29, 2003, and the entire contents of all of which are hereby incorporated by reference herein.

This application relates to a dissecting tip for a surgical stapling device.

SUMMARY

In accordance with the present disclosure, a dissecting tip is provided for use with a surgical stapling device and, especially, a linear surgical stapling device, including an end effector having an anvil assembly and a cartridge assembly. The dissecting tip is supported on the end effector, and may be supported on the distal end of the anvil assembly. The dissecting tip may instead or also be supported on the distal end of the cartridge assembly. The dissecting tip may be positioned to extend distally from the anvil assembly and includes a body having an outer surface, an inner surface and a distal tip. The body may assume a variety of configurations. For example, the body may include inner and/or outer surfaces which are curved along the longitudinal and/or transverse axis of the anvil assembly and extend downwardly towards the cartridge assembly. In another embodiment, the inner and/or outer surfaces are substantially flat. In yet another embodiment, the inner and/or outer surfaces include a pair of flat sections interconnected by a curved transition section. In yet another embodiment, the body may include a distal portion having a distal tip having circular cross-section. The width of the dissecting tip may decrease from the proximal end of the dissecting tip to the distal end of the dissecting tip. The distal tip of the dissecting tip may also be rounded and/or blunt to prevent snagging, pulling and/or cutting of tissue.

The dissecting tip functions to dissect or separate target tissue and certain tissue. As discussed above, "certain tissue" includes adherent, connective, joined or other tissue. This may be accomplished by passing or pressing the outer surface of dissecting tip against the target tissue and pushing the distal tip of the dissecting tip behind the certain tissue such that the certain tissue is positioned adjacent the inner surface of the dissecting tip. The dissecting tip may be located and dimensioned to permit access through a trocar cannula assembly which is sized to receive a surgical stapling instrument without a dissecting tip.

BRIEF DESCRIPTION OF THE DRAWINGS

Various embodiments of the presently disclosed dissecting tip are described herein with reference to the drawings, wherein:

FIG. 1 is a side top perspective view of a surgical stapling device including one embodiment of the presently disclosed dissecting tip attached to the end effector thereof;

FIG. 2 is an enlarged view of the indicated area of detail shown in FIG. 1;

FIG. 5a is a top view of the dissecting tip and end effector of the surgical stapling device shown in FIG. 1;

FIG. 5b is a bottom view of the dissecting tip and end effector shown in FIG. 5a;

FIG. 5c is a front view of the dissecting tip and end effector shown in FIG. 5b;

FIG. 5d is a side perspective view from the front of the presently disclosed dissecting tip dissector shown in FIG. 1;

FIG. 5e is a side view of the dissecting tip shown in FIG. 5d;

FIG. 6b is a top view of the dissecting tip and end effector of the surgical stapling device shown in FIG. 6;

FIG. 6c is a bottom view of the dissecting tip and end effector shown in FIG. 6b;

FIG. 6d is a front view of the dissecting tip and end effector shown in FIG. 6c;

FIG. 6e is a side top perspective view from the front of the presently disclosed dissecting tip shown in FIG. 6;

FIG. 6f is a side view of the dissecting tip shown in FIG. 6e;

FIG. 7f is a side view of the dissecting tip shown in FIG. 7e;

FIG. 8b is a top view of the dissecting tip and end effector of the surgical stapling device shown in FIG. 8;

FIG. 8c is a bottom view of the dissecting tip and end effector shown in FIG. 8b;

FIG. 8d is a front view of the dissecting tip and end effector shown in FIG. 8c;

FIG. 8e is a side perspective view from the front of the presently disclosed dissecting tip shown in FIG. 8;

FIG. 8f is a side perspective view from the rear of the dissecting tip shown in FIG. 8e;

FIG. 8g is a side view of the dissecting tip shown in FIG. 8e;

FIG. 9b is a top view of the dissecting tip and end effector of the surgical stapling device shown in FIG. 9;

FIG. 9c is a bottom view of the dissecting tip and end effector shown in FIG. 9b;

FIG. 9d is a front view of the dissecting tip and end effector shown in FIG. 9c;

FIG. 9e is a side perspective view from the front of the presently disclosed dissecting tip shown in FIG. 9;

FIG. 9f is a side view of the dissecting tip shown in FIG. 9e;

FIG. 10b is a top view of the dissecting tip and end effector of the surgical stapling device shown in FIG. 10;

FIG. 10c is a bottom view of the dissecting tip and end effector shown in FIG. 10b;

FIG. 10d is a front view of the dissecting tip and end effector shown in FIG. 10c;

FIG. 10e is a side perspective view from the front of the presently disclosed dissecting tip shown in FIG. 10;

FIG. 10f is a side view of the dissecting tip shown in FIG. 10e;

FIG. 11b is a top view of the dissecting tip and end effector of the surgical stapling device shown in FIG. 11;

FIG. 11c is a bottom view of the dissecting tip and end effector shown in FIG. 11b;

FIG. 11d is a front view of the dissecting tip and end effector shown in FIG. 11c;

FIG. 11e is a side perspective view from the front of the presently disclosed dissecting tip shown in FIG. 11;

FIG. 11f is a side view of the dissecting tip shown in FIG. 11e;

FIG. 12b is a top view of the dissecting tip and end effector of the surgical stapling device shown in FIG. 12;

FIG. 12c is a bottom view of the dissecting tip and end effector shown in FIG. 12b;

FIG. 12d is a front view of the dissecting tip and end effector shown in FIG. 12c;

FIG. 12e is a side perspective view from the front of the presently disclosed dissecting tip shown in FIG. 12;

FIG. 12f is a side view of the dissecting tip shown in FIG. 12e;

FIG. 13c is a top view of the end effector and dissecting tip shown in FIG. 13a;

FIG. 13d is a bottom view of the end effector and dissecting tip shown in FIG. 13a;

FIG. 13e is a front view of the end effector and dissecting tip shown in FIG. 13a;

FIG. 13f is a side view of the end effector and dissecting tip shown in FIG. 13a;

FIG. 14c is a top view of the end effector and dissecting tip shown in FIG. 14a;

FIG. 14d is a bottom view of the end effector and dissecting tip shown in FIG. 14a;

FIG. 14e is a front view of the end effector and dissecting tip shown in FIG. 14a;

FIG. 14f is a side view of the end effector and dissecting tip shown in FIG. 14a;

FIG. 16b is a top view of the end effector and dissecting tip shown in FIG. 16a;

FIG. 16c is a bottom view of the end effector and dissecting tip shown in FIG. 16a;

FIG. 16d is a front view of the end effector and dissecting tip shown in FIG. 16a;

FIG. 16e is a side perspective view from above of the dissecting tip shown in FIG. 16a;

FIG. 17b is a top view of the end effector and dissecting tip shown in FIG. 17a;

FIG. 17c is a bottom view of the end effector and dissecting tip shown in FIG. 17a;

FIG. 17d is a front view of the end effector and dissecting tip shown in FIG. 17a; and FIG. 17e is a side perspective view from above of the dissecting tip shown in FIG. 17a.

DETAILED DESCRIPTION OF EMBODIMENTS

Figure 3:
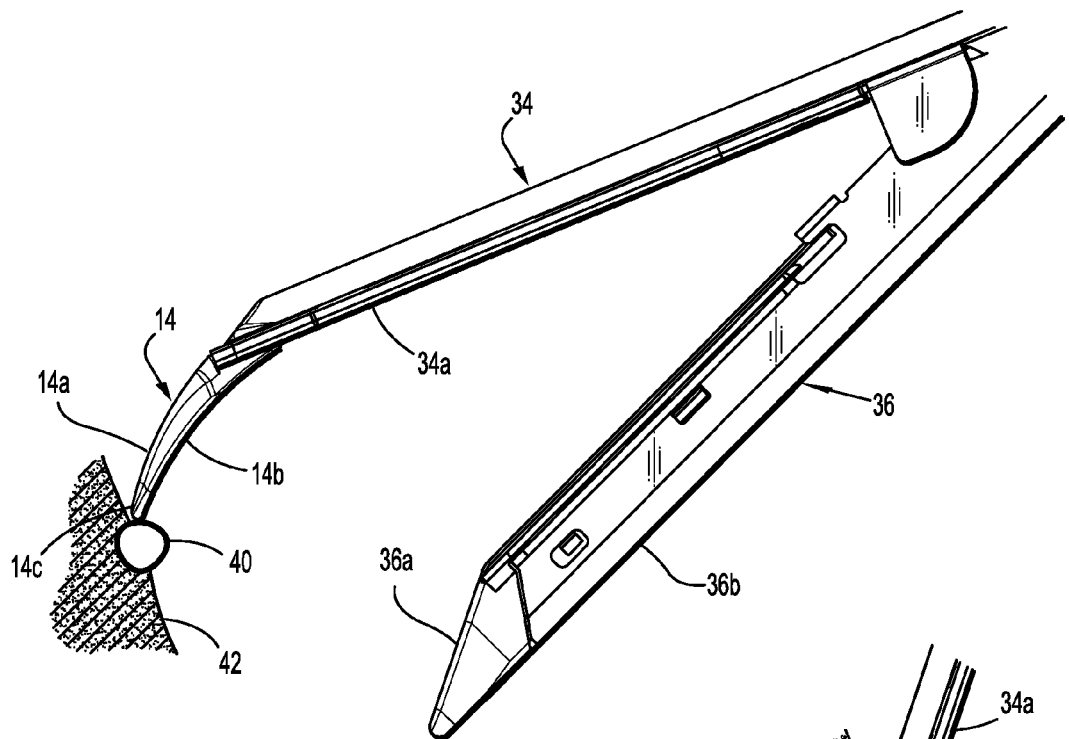
FIG. 3 is a side view of the end effector with portions broken away and of the dissecting tip of the surgical stapling device shown in FIG. 1 with the end effector in the open position adjacent target tissue and certain tissue which is adhered to the target tissue.

Embodiments of the presently disclosed surgical stapling device with dissecting tip will now be described in detail with reference to the drawings wherein like reference numerals designate identical or corresponding elements in each of the several views.

In the description that follows, the term "proximal", as is traditional, will refer to the end of the stapling device closest the operator and the term "distal" will refer to the end of the stapling device furthest from the operator.

FIG. 1 illustrates a linear surgical stapling device shown generally as 10 including an end effector 12 having one embodiment of the presently disclosed dissecting tip, here generally designated 14, supported thereon. Stapling device 10 also includes a handle assembly 16 and an endoscopic portion 18. End effector 12 forms part of a disposable loading unit or single use loading unit (SULU) 20. With the exception of dissecting tip 14, the remaining components of surgical stapling device 10 are substantially as known in the art described in U.S. Pat. Nos. 5,865,361 ("'361 patent"), 6,079,606, 6,241,139, 6,330,965 and 6,669,073. It is contemplated that the presently disclosed embodiments of the dissecting tip may be used in association with other known linear stapling devices of both endoscopic and open construction. These devices include articulating and non-articulating devices as well as reusable and non-reusable devices. Examples of such devices are disclosed in U.S. Pat. Nos. 6,202,914, 6,250,532, 6,109,500, 6,032,849, 5,584,425, 5,540,375, 5,554,169, 5,507,426, 5,482,197. In light of the comments above, only the embodiments of the dissecting tips disclosed herein will be discussed in detail in this application.

FIGS. 1-5c illustrate one embodiment of the presently disclosed dissecting tip in combination with a surgical stapling device 10. As discussed above, surgical stapling device 10 includes a handle assembly 16, an elongated body or endoscopic portion 18, and a SULU 20. Briefly, handle assembly 16 includes a stationary grip member 22, a pivotable trigger 24, an articulation lever 26, a rotation knob 27 and return knobs 28. SULU 20 is adapted to be releasably attached to elongated body portion 18 and includes a proximal body portion 32 and end effector 12. End effector 12 is pivotally attached to proximal body portion 32 to facilitate articulation of end effector 12 in relation to proximal body portion 32.

End effector 12 includes an anvil assembly 34 and a cartridge assembly 36 which houses a plurality of linear rows of staples. Anvil assembly 34 and cartridge assembly 36 are movable, here, pivotal in relation to each other between an open position and a clamped or approximated position. Pivotable trigger 24 is actuable through an actuation stroke or strokes to move anvil assembly 34 in relation to cartridge assembly 36 between the open position and the clamped position and to eject staples from cartridge assembly 36. The operation of each of these components is described in greater detail in the '361 patent and will not be discussed in further detail herein.

Dissecting tip 14 is secured to a distal end of the end effector 12. Alternately, dissecting tip may be integrally formed with end effector 12 or end effector 12 and dissecting tip 14 may be of monolithic construction. In one preferred embodiment, dissecting tip 14 is secured to a distal surface of anvil assembly 34 which is contiguous with a tissue contact surface 34a of anvil assembly 34. Dissecting tip 14 may be formed from a surgical grade metal or plastic and attached to anvil assembly 34 using any known suitable fastening technique, e.g., adhesives, welding, soldering, brazing, pins, etc. Alternately, other known surgically approved materials may be used to construct dissecting tip 14. In this embodiment, dissecting tip 14 includes a curved inner surface 14a and a curved outer surface 14b and a tip 14c. In one embodiment, curved inner surface 14a and curved outer surface 14b are smooth. Smooth surfaces prevent dissecting tip 14 from snagging, pulling and/or cutting tissue. In one embodiment, tip 14c is thin and blunt. The width of dissecting tip 14 decreases from its proximal end to its distal end and, in one embodiment, the width of dissecting tip 14 decreases substantially continuously from its proximal end to its distal end culminating at tip 14c. The width of dissecting tip 14 at its proximal end (i.e. its greatest width) is smaller than the width of cartridge assembly 36. In one embodiment, tip 14c is generally circular. Generally circular tip 14c has a diameter of from about 3 to about 6 mm. In one embodiment, tip 14c has a diameter of from about 3 to about 4 mm. In an alternative embodiment, tip 14c has a diameter of from about 5 to about 6 mm. Curved inner surface 14a is formed by any suitable radius, for example a one inch radius. Curved inner surface may be formed by a plurality of curved radii. In one embodiment, curved inner surface 14a of dissecting tip 14 extends downwardly towards cartridge assembly 36 from the horizontal plane of anvil assembly 34. In one embodiment, curved inner surface 14a of dissecting tip 14 extends downwardly at an angle of from about 30 to about 90 degrees from the horizontal surface of anvil assembly 34. In alternate embodiments, curved inner surface extends downwardly at an angle of from about 50 to about 90 degrees, from about 60 to about 80 degrees and from about 80 to about 90 degrees. In one embodiment, the distance from tip 14c to the horizontal plane of anvil assembly 34 is from about 10 to about 30 mm. In alternative embodiments, the distance from tip 14c to the horizontal plane of anvil assembly 34 is about 10 mm and, alternatively, is from about 25 to about 30 mm. Inner surface 14a of dissecting tip 14 extends downwardly toward cartridge assembly 36 to a location beyond the distal end of cartridge assembly 36. By extending dissecting tip 14 beyond cartridge assembly 36, access to adherent tissue is improved and visualization of dissecting tip 14 to confirm proper position and that dissection of the adherent tissue is completed is permitted. In one embodiment, there are substantially smooth bends or transitions from dissecting tip 14 to the portion(s) of the anvil assembly 34 from which dissecting tip 14 is secured or from which it extends. When anvil assembly 34 and cartridge assembly 36 are in the clamped or approximated position, dissecting tip 14 is spaced from a distal angled tissue guide surface 36a of cartridge assembly 36. In one embodiment, the space between dissecting tip 14 and distal angled surface guide 36a is at least the same as or greater than (in one embodiment two times greater) than the gap between the tissue contacting surfaces of the anvil assembly 34 and the cartridge assembly 36 when they are approximated. However, there may be instances when it is desired to have less space between the dissecting tip and tissue guide surface 36a of cartridge assembly 36.

Figure 4:
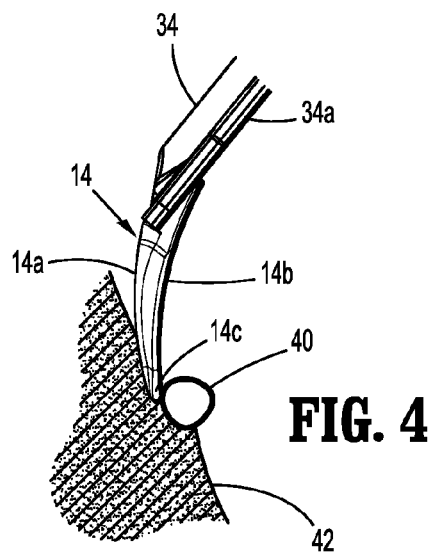
FIG. 4 is a side view of the anvil assembly shown in FIG. 3 with the dissecting tip positioned partially between the certain tissue and the target tissue.
Figure 4A:
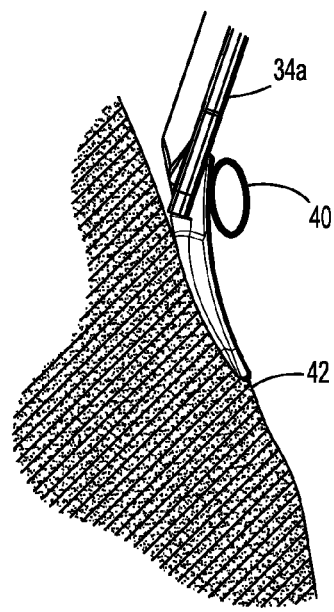
FIG. 4a is a side view of the anvil assembly and dissecting tip shown in FIG. 4 positioned fully between the certain tissue and the target tissue.
Figure 5:
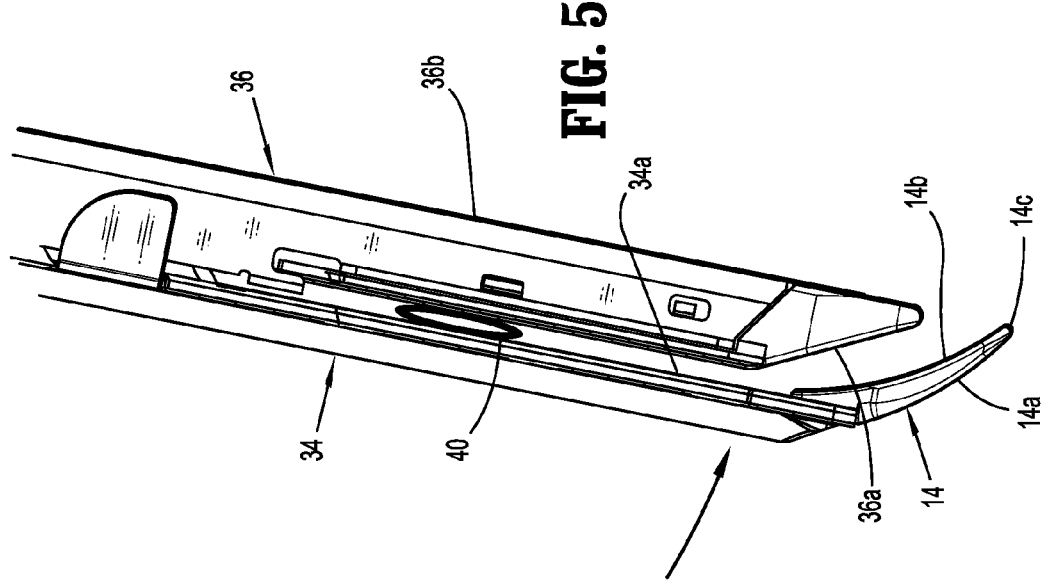
FIG. 5 is a side view of the dissecting tip and end effector shown in FIG. 4b with certain tissue positioned between a clamped anvil assembly and cartridge assembly.
Figure 4B:
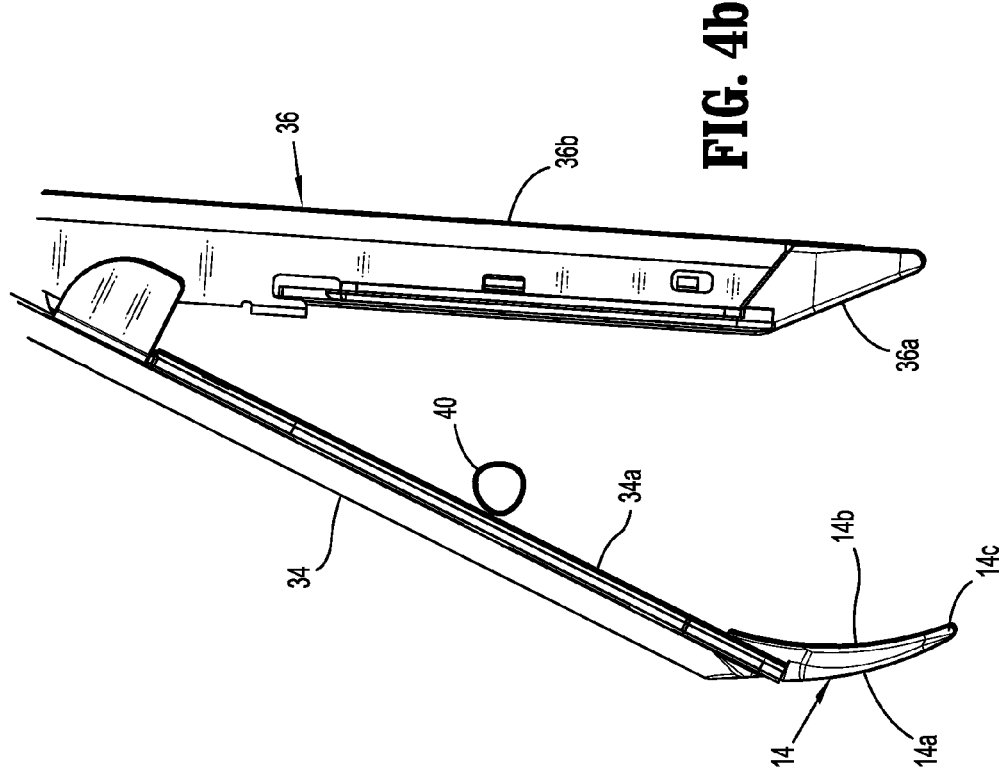
FIG. 4b is a side view of the dissecting tip and end effector shown in FIG. 3 with certain tissue positioned between an open anvil assembly and cartridge assembly.

Referring now to FIGS. 3-5, when surgical stapling device 10 is used to dissect certain tissue 40, e.g., blood or airway vessels, from target tissue 42, e.g., stomach, lung, etc., curved outer surface 14b of dissecting tip 14 can be pressed or passed against target tissue 42 and slid behind certain tissue 40, e.g., adherent, tissue to separate and/or dissect tissue 40 from, for example, adherence with target tissue 42. Positioning of dissecting tip 14 behind certain tissue 40 may be accomplished with anvil assembly 34 and cartridge assembly 36 in the open position. Alternately, the anvil and cartridge assemblies can be moved to the clamped position to provide extra stability to the end effector during dissection of tissue. Thereafter, either or both of certain tissue 40 and target tissue 42 can be independently joined and cut by clamping and actuating surgical stapling device 10.

It is noted that although not described in detail, end effector 12 may be adapted to access the surgical site through a trocar cannula assembly as is known in the art. To accomplish this, anvil assembly 34 and cartridge assembly 36 are maintained in a clamped position as elongated body portion 18 and end effector 12 are inserted through the cannula (not shown). As illustrated, dissecting tip 14 does not extend below a plane defined by a bottom surface 36b of cartridge assembly 36, nor does dissecting tip 14 extend outwardly beyond the sidewalls of cartridge assembly 36. The dissecting tip can be above, e.g., slightly above the plane. As such, surgical stapling device 10 including dissecting tip 14 may be used with a trocar cannula assembly sized to receive a surgical stapling device not having a dissecting tip 14.

Figure 6:
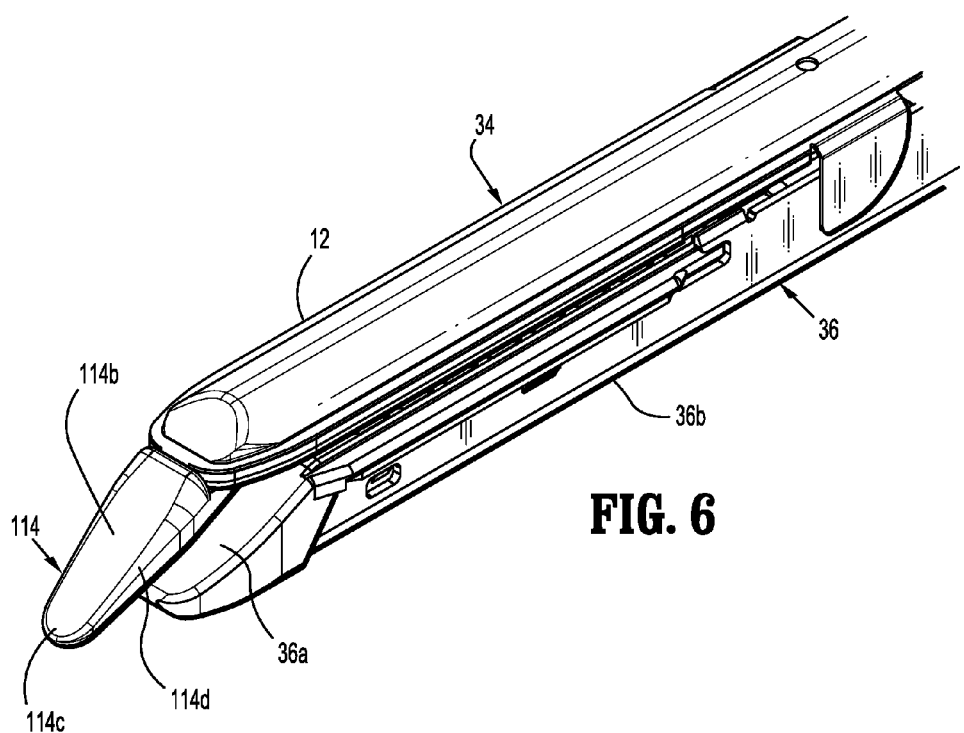
FIG. 6 is an enlarged top side perspective view from the front of the end effector of a surgical stapling device including another embodiment of the presently disclosed dissecting tip.
Figure 6A:
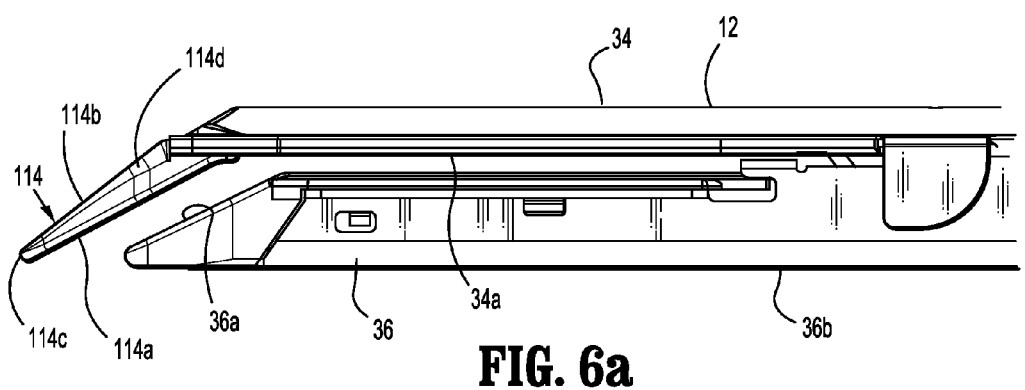
FIG. 6a is a side view of the dissecting tip and end effector shown in FIG. 6.

FIGS. 6-6e illustrate another embodiment of the presently disclosed dissecting tip shown generally as 114. Dissecting tip 114 is secured to the distal end of end effector 12. Alternately, dissecting tip 114 may be monolithically or integrally formed with end effector 12. As discussed above, end effector 12 includes anvil assembly 34 and cartridge assembly 36. Dissecting tip 114 is secured to a distal surface or portion of anvil assembly 34 in the manner described above with respect to dissecting tip 14. Dissecting tip 114 is also constructed from a surgical grade metal Dissecting tip 114 is also constructed from a surgical grade metal or plastic. The use of other known surgically approved materials to construct dissecting tip 114 is envisioned. Dissecting tip 114 includes substantially flat inner and outer surfaces, 114a and 114b, respectively and tip 114c. In one embodiment, substantially flat inner surface 114a and substantially flat outer surface 114b are smooth. Smooth surfaces prevent dissecting tip 114 from snagging, pulling and/or cutting tissue. In one embodiment, tip 114c is thin and blunt. The width of dissecting tip 114 decreases from its proximal end to its distal end and, in one embodiment, the width of dissecting tip 114 decreases substantially continuously from its proximal end to its distal end culminating at tip 114c. The width of dissecting tip 114 at its proximal end (i.e. its greatest width) is smaller than the width of cartridge assembly 36. In one embodiment, tip 114c is generally circular. Generally circular tip 114c has a diameter of from about 3 to about 6 mm. In one embodiment, tip 114c has a diameter of from about 3 to about 4 mm. In an alternative embodiment, tip 114c has a diameter of from about 5 to about 6 mm. In one embodiment, inner surface 114a of dissecting tip 114 extends downwardly towards cartridge assembly 36 from the horizontal plane of anvil assembly 34. In one embodiment, inner surface 114a of dissecting tip 114 extends downwardly at an angle of from about 5 to about 90 degrees from the horizontal surface of anvil assembly 34. In alternate embodiments, inner surface 114a extends downwardly at an angle of from about 30 to about 90, from about 50 to about 90 degrees, from about 60 to about 80 degrees and from about 80 to about 90 degrees. In one embodiment, the distance from tip 114c to the horizontal plane of anvil assembly 34 is from about 10 to about 30 mm. In alternative embodiments, the distance from tip 114c to the horizontal plane of anvil assembly 34 is about 10 mm and, alternatively, is from about 25 to about 30 mm. Inner surface 114a of dissecting tip 114 extends downwardly toward cartridge assembly 36 to a location beyond the distal end of cartridge assembly 36. In one embodiment, tip 114c does not extend below a plane defined by a bottom surface 36b of cartridge assembly 36. As such, a surgical stapling device including dissecting tip 114 can be inserted through a trocar cannula assembly sized to receive the stapling device. In an alternative embodiment, tip 114c extends below the plane defined by the bottom surface 36b of cartridge assembly 36. When anvil assembly 34 and cartridge assembly 36 are in the clamped or approximated position, inner surface 114a of dissecting tip 114 is spaced from a distal angled tissue guide surface 36a of cartridge assembly 36 and, in one embodiment, it is spaced substantially parallel from tissue guide surface 36a. In one embodiment, the space between dissecting tip 114 and distal angled surface guide 36a is at least the same as or greater than (in one embodiment two times greater) than the gap between the tissue contacting surfaces of the anvil assembly 34 and the cartridge assembly 36 when they are approximated. However, there may be instances when it is desired to have less space between the dissecting tip and tissue guide surface 36a of cartridge assembly 36.

The use of dissecting tip 114 is substantially identical to that of dissecting tip 14 and will not be discussed in further detail herein.

Figure 7:
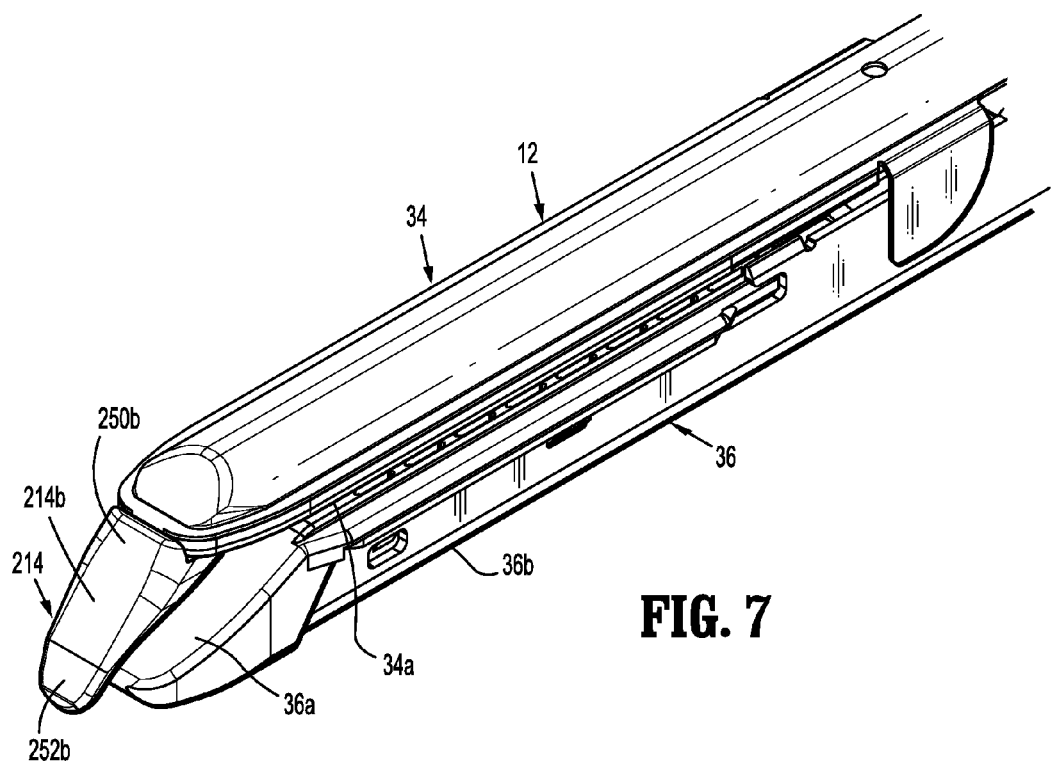
FIG. 7 is an enlarged side top perspective view from the front of the end effector of a surgical stapling device including another embodiment of the presently disclosed dissecting tip.
Figure 7A:
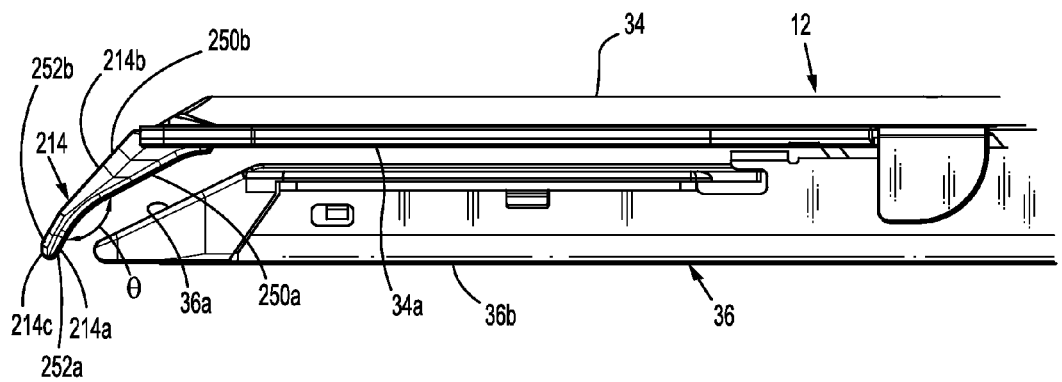
FIG. 7a is a side view of the dissecting tip and end effector shown in FIG. 7.
Figure 7B:
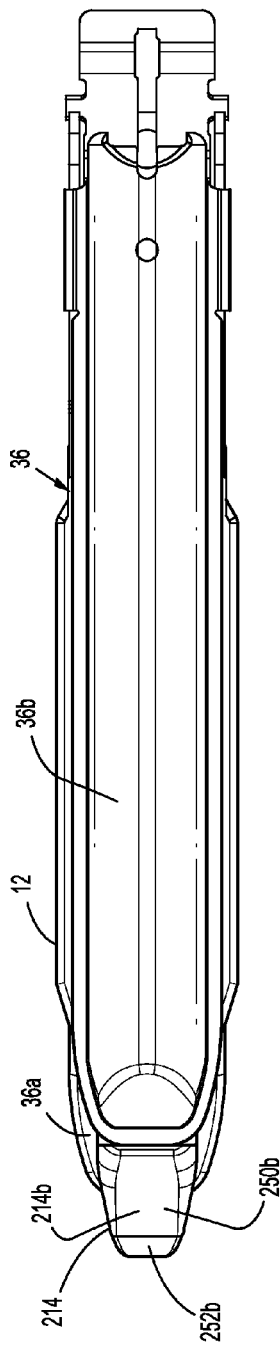
FIG. 7b is a top view of the dissecting tip and end effector of the surgical stapling device shown in FIG. 7.
Figure 7C:
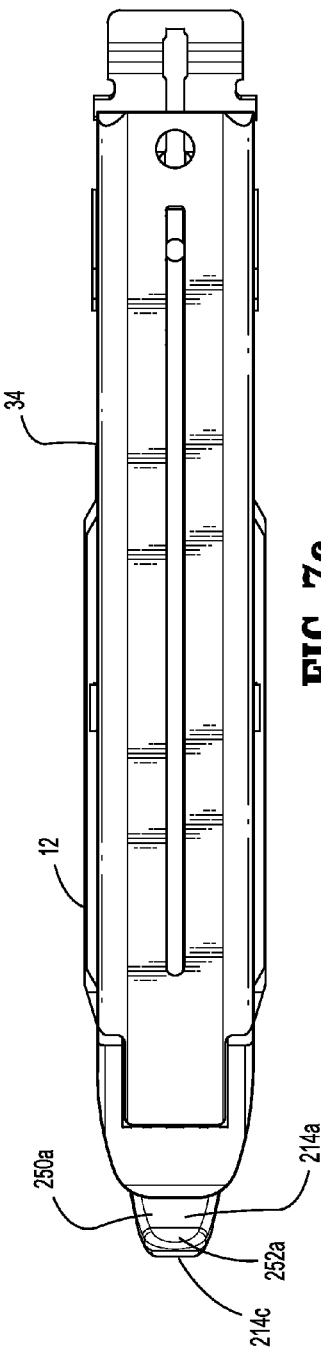
FIG. 7c is a bottom view of the dissecting tip and end effector shown in FIG. 7b.
Figure 7D:
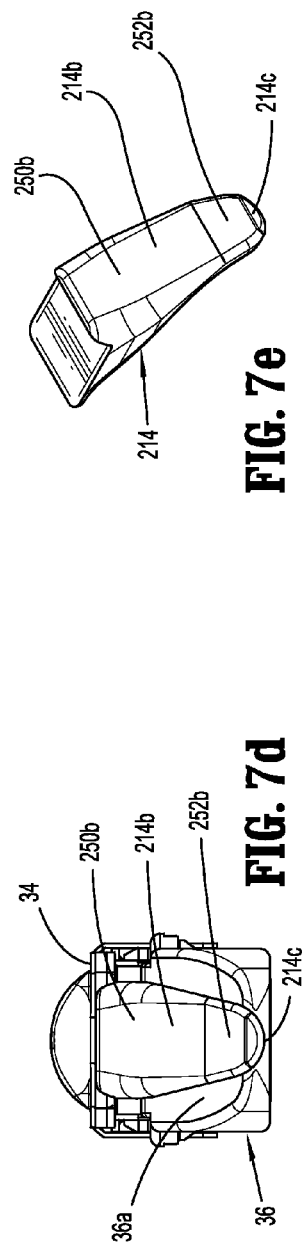
FIG. 7d is a front view of the dissecting tip and end effector shown in FIG. 7c.
Figure 7E:
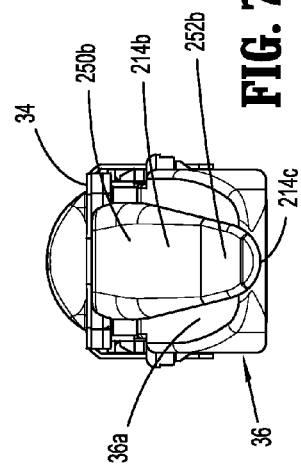
FIG. 7e is a side top perspective view from the front of the presently disclosed dissecting tip shown in FIG. 7.

FIGS. 7-7e illustrate yet another embodiment of the presently disclosed dissecting tip shown generally as 214. Dissecting tip 214 is secured to anvil assembly 34 of end effector 12 in the manner described above with respect to dissecting tip 14. Dissecting tip 214 is also constructed from a surgical grade metal or plastic. Alternatively, the use of other known materials of construction is envisioned.

Dissecting tip 214 includes inner and outer surfaces 214a and 214b and a blunt tip 214c. Inner and outer surfaces 214a and 214b each have a substantially flat proximal portion 250a and 250b and a substantially flat distal portion 252a and 252b positioned at an angle to proximal portion 250. In one embodiment, proximal portion 250 and distal portion 252, along inner surface 214a, define an angle θ (FIG. 7a) of between about 90° and about 170°. In one embodiment, angle θ is about 30°. The transition between proximal portion 250a and distal portion 252a is smooth and rounded to prevent snagging, pulling and/or cutting of tissue. The outer surface of tip 214 can have other shapes, e.g., rounded as in FIGS. 1-5e. As discussed above with respect to dissecting tips 14 and 114, the width of dissecting tip 214 decreases from its proximal end to its distal end and at its greatest width is less than the width of cartridge assembly 36. The distal end of distal portion 252a includes a blunt tip 214c which in this embodiment does not extend beyond a plane defined by a bottom surface 36b of cartridge assembly 36. The use of dissecting tip 214 is substantially identical to that of dissecting tip 14 and will not be discussed in further detail herein.

Figure 8:
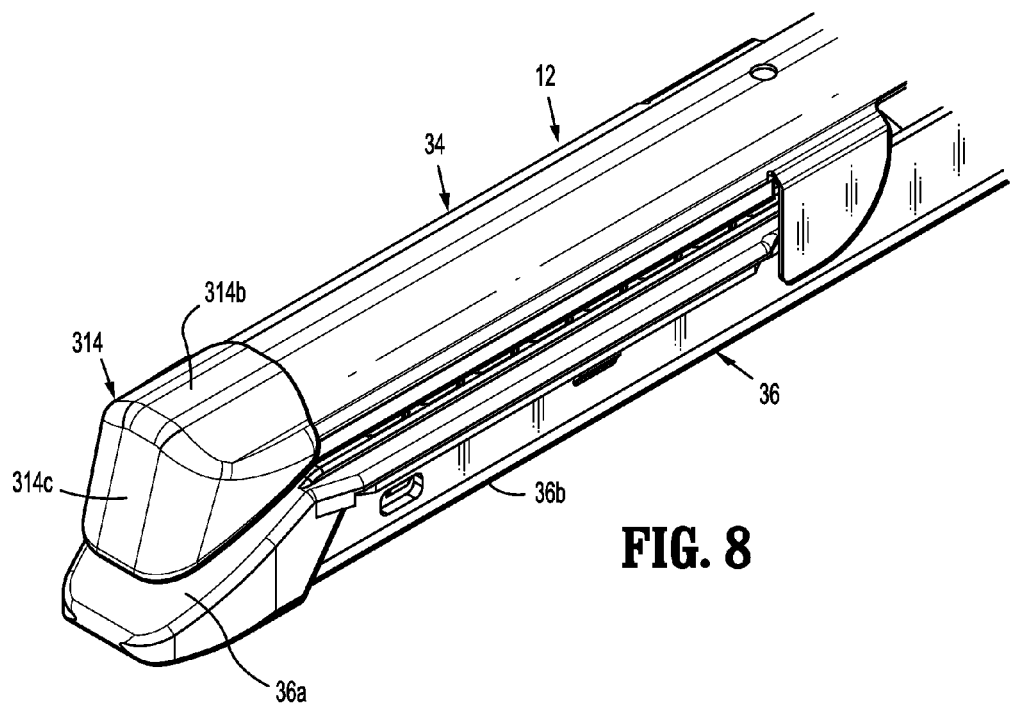
FIG. 8 is an enlarged side perspective view from the front of the end effector of a surgical stapling device including yet another embodiment of the presently disclosed dissecting tip.
Figure 8A:
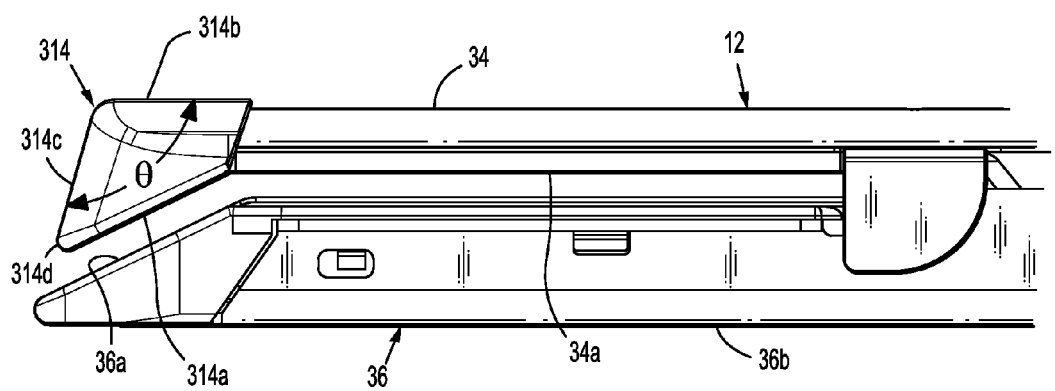
FIG. 8a is a side view of the dissecting tip and end effector shown in FIG. 8.

FIGS. 8-8e illustrate another embodiment of the presently disclosed dissecting tip shown generally as 314. Dissecting tip 314 includes an inner surface 314a, a top surface 314b and a front surface 314c Inner surface 314a is angled and is substantially parallel to distal angled tissue guide surface 36a of cartridge assembly 36. Top surface 314b is curved or concave along an axis transverse to a longitudinal axis of anvil assembly 34. Front surface 314c is angled downwardly towards cartridge assembly 36 and defines an angle θ (FIG. 8a) of between about 95° and 135° with respect to the longitudinal axis of anvil assembly 34. In one embodiment, angle θ is about 106°. The width of dissecting tip 314 decreases from a proximal end of dissecting tip 314 to the distal end of dissecting tip 314. The width at the proximal end of dissecting tip 314 is approximately equal to the width of cartridge assembly 36. As discussed above, the dimensions and positioning of dissecting tip 314 on stapling device 10 permit positioning of stapling device 10 through a trocar cannula assembly sized to allow passage stapling device 10 without dissecting tip 314.

Distal tip 314d of dissecting tip 314 may be positioned proximally of the distal end of cartridge assembly 36. Alternately, distal tip 314d may be positioned adjacent to or distally of the distal end of cartridge assembly 36.

Dissecting tip 314 includes a substantially hollow recess 314e (FIG. 8f) which is configured to receive the distal end of anvil assembly 34. Dissecting tip 314 may be positioned over the distal end of anvil assembly 34 and secured thereto using any known fastening technique, e.g., adhesives, welding, friction fit, pins, screws, etc. Dissecting tip 314 may be formed from surgical grade metals or plastics although other known materials of construction are envisioned. Dissecting tip 314 functions basically in the same manner as discussed above with respect to dissecting tip 14 and will not be discussed in further detail herein.

Figure 9:
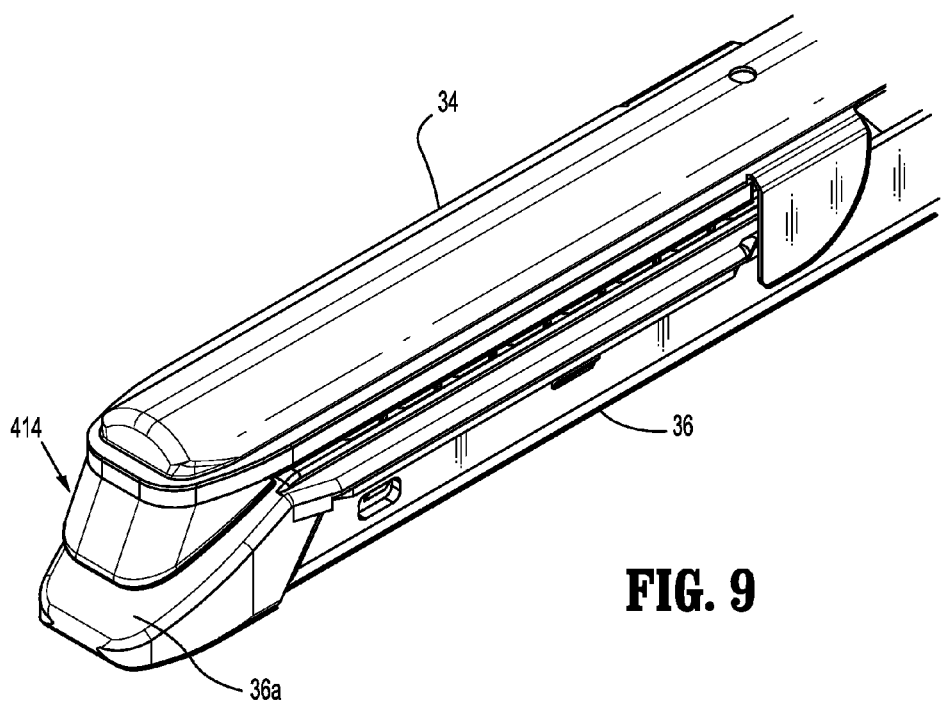
FIG. 9 is an enlarged top side perspective view from the front of the end effector of a surgical stapling device including another preferred embodiment of the presently disclosed dissecting tip.
Figure 9A:
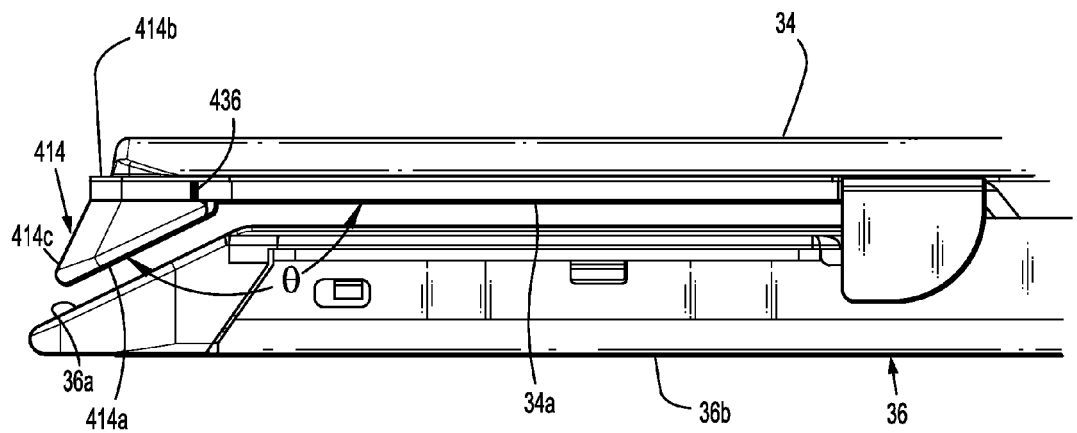
FIG. 9a is a side view of the dissecting tip and end effector shown in FIG. 9.

FIGS. 9-9e illustrate yet another embodiment of the presently disclosed dissecting tip shown generally as 414. Dissecting tip 414 is similar in shape to dissecting tip 314 but includes a peg extension 436 (FIG. 9e) to secure dissecting tip 414 to anvil assembly 34, rather than a hollow recess as will be further discussed below. Dissecting tip 414 includes an inner surface 414a, a top surface 414b, and a front surface 414c. Inner surface 414a is substantially parallel to a tissue guide surface 36b on the distal end of cartridge assembly 36. Top surface 414b is flat and is positioned to abut against a distal surface of anvil assembly 34 which is contiguous with an inner tissue engaging surface 34a of anvil assembly 34. Front surface 414c is angled downwardly towards cartridge assembly 36 and in one embodiment defines an angle θ (FIG. 9a) of between about 95° and about 135°. In one embodiment, angle θ is about 154°.

Peg extension 436 is a T-shaped member which extends upwardly from a proximal end of top surface 414b of dissecting tip 414. The upper portion 452 of T-shaped member 436 extends transversely across anvil assembly 34 and is dimensioned to be received in a linear slot (not shown) formed in the distal end of anvil assembly 34. To attach dissecting tip 414 to anvil assembly 34, upper portion 452 of T-shaped member 436 is positioned within the distal linear slots of anvil assembly 34 and dissecting tip 414 is rotated 90° to lock upper portion 452 within the linear slot and lock dissecting tip to anvil assembly 34. Additional fastening techniques may be used to fixedly secure dissecting tip 414 to anvil assembly 34, e.g., adhesives, welding, etc.

Figure 10:
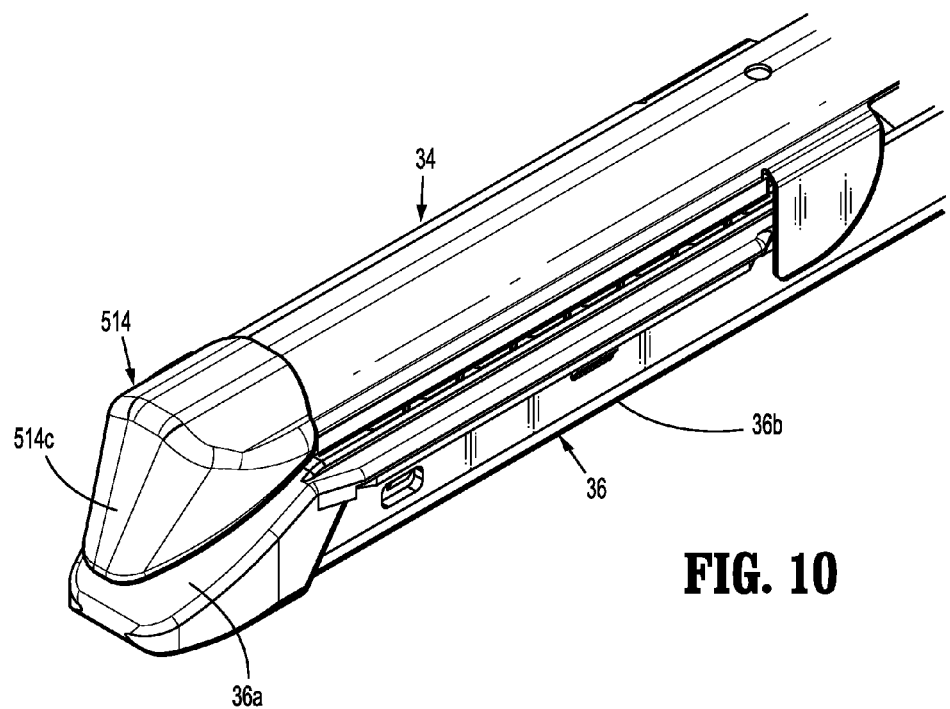
FIG. 10 is an enlarged side perspective view from the front of the end effector of a surgical stapling device including another embodiment of the presently disclosed dissecting tip.
Figure 10A:
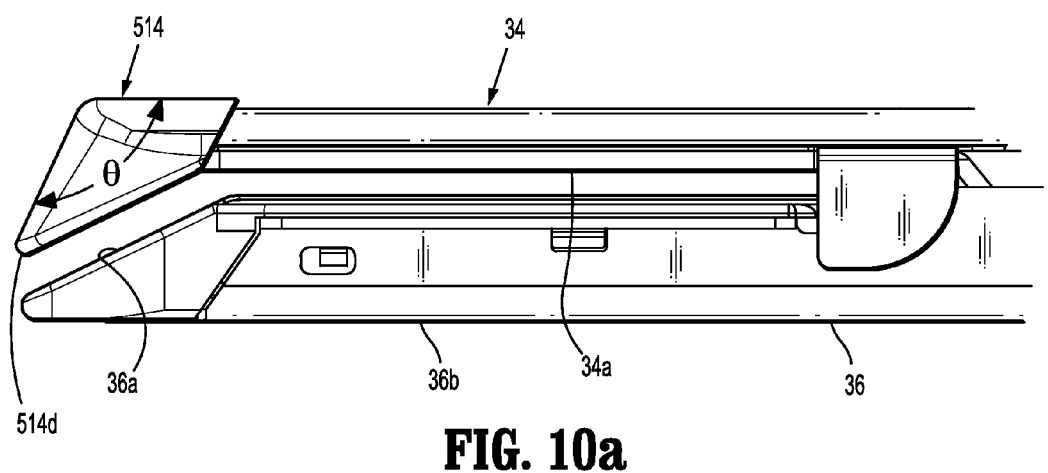
FIG. 10a is a side view of the dissecting tip and end effector shown in FIG. 10.

FIGS. 10-10e illustrate another embodiment of the presently disclosed dissecting tip shown generally as 514. Dissecting tip 514 is substantially similar to dissecting tip 314 in construction but differs in that a distal tip 514d of dissecting tip 514 is narrower than and positioned above, over or adjacent to the distal end of cartridge assembly 36. Further, top surface 514b and front surface 514c together define an angle θ (FIG. 10a) of between about 95° and about 135°. In one embodiment, angle θ is about 115°. As discussed above with respect to dissecting tip 314, dissecting tip 514 defines a hollow recess (not shown) dimensioned and configured to receive the distal end of anvil assembly 34.

Figure 11:
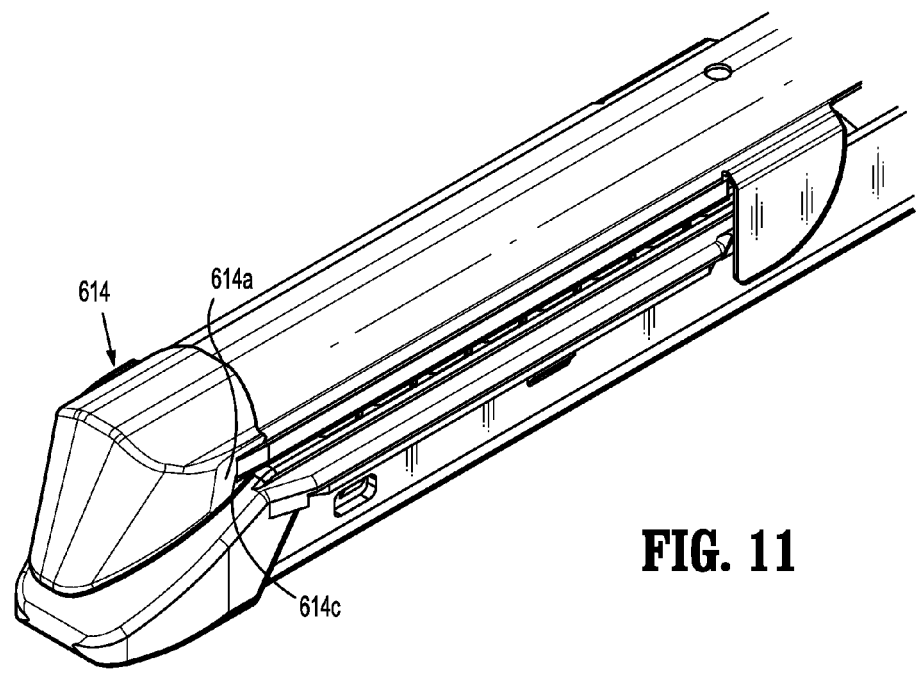
FIG. 11 is an enlarged side perspective view from the front of the end effector of a surgical stapling device including another embodiment of the presently disclosed dissecting tip.
Figure 11A:
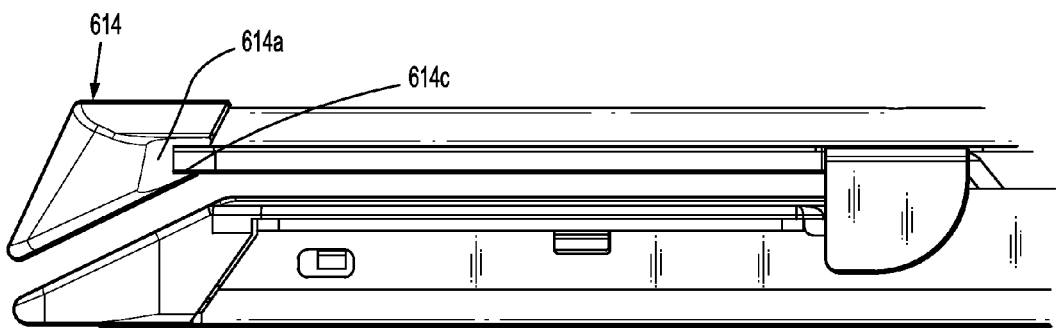
FIG. 11a is a side view of the dissecting tip and end effector shown in FIG. 11.

FIGS. 11-11e illustrate yet another embodiment of the presently disclosed dissecting tip shown generally as 614. Dissecting tip 614 is substantially similar to dissecting tip 514 with the exception that dissecting tip 614 includes a pair of cutouts 614c formed in opposite tapered sidewalls 614a and 614b thereof. The tapered sidewalls 614a and 614b and cutouts 614c provide a smooth transition from dissecting tip 614 to anvil assembly 34 to prevent snagging and pulling of tissue.

Figure 12:
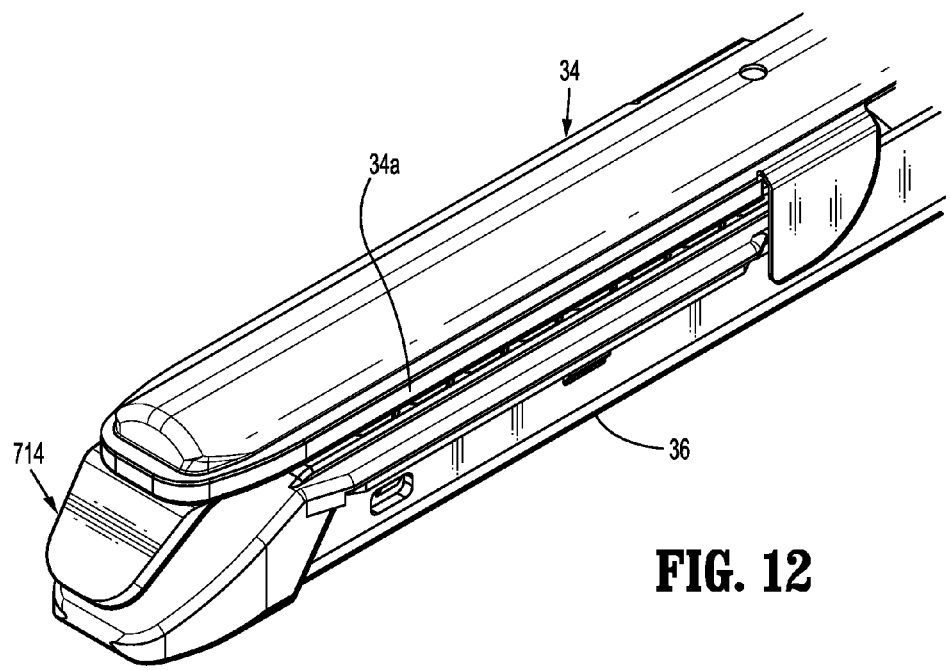
FIG. 12 is an enlarged side top perspective view from the front of the end effector of a surgical stapling device including another embodiment of the presently disclosed dissecting tip.

FIG. 12-12e illustrate another embodiment of the presently disclosed dissecting tip shown generally as 714. Dissecting tip 714 is formed integrally and/or monolithically with an anvil plate 34a (FIG. 12e) of anvil assembly 34 and is therefore formed from a surgical grade metal. Dissecting tip 714 includes an inner surface 714a, an outer surface 714b and a distal tip 714c which may be rounded. Inner and outer surfaces 714a and 714b are substantially flat and define an angle θ of between about 105° and about 155° in relation to a longitudinal axis of anvil assembly 34. In one embodiment, θ is about 136° Dissecting tip 714 extends downwardly towards cartridge assembly 36, at angle θ which in one embodiment is less than an angle B defined between tissue guide surface 36a formed on the distal end of cartridge assembly 36 and a longitudinal axis of cartridge assembly 36. Although the dissecting tip of this disclosure can be employed on any sized SULU or end effector, for some applications shorter end effectors may be preferred.

Figure 12A:
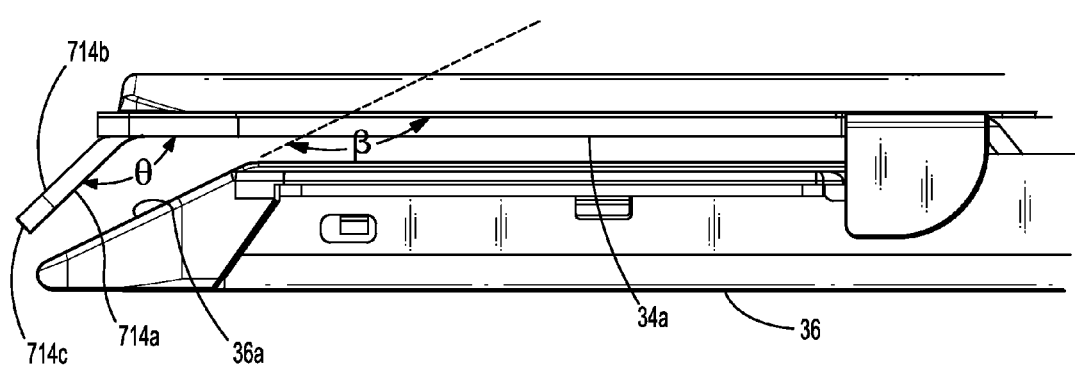
FIG. 12a is a side view of the dissecting tip and end effector shown in FIG. 12.

The junction, blend or transition of the proximal portion of the inner surface of dissecting tip 14 with the plane of tissue contacting surface 34 of the anvil assembly may be positioned axially distal of the junction, blend or transition of tissue guide surface 36a and the tissue contacting surface of cartridge assembly 36. This provides space to allow tissue to be squeezed distally of the staple working portions of the tissue contacting surfaces of anvil assembly 34 and cartridge assembly 36 and helps maintain the desired tissue gap between those surfaces, during approximation and clamping. The configuration of dissecting tip 714 of end effector 12 shown in FIG. 12a exemplifies this junctional relationship.

Figure 13:
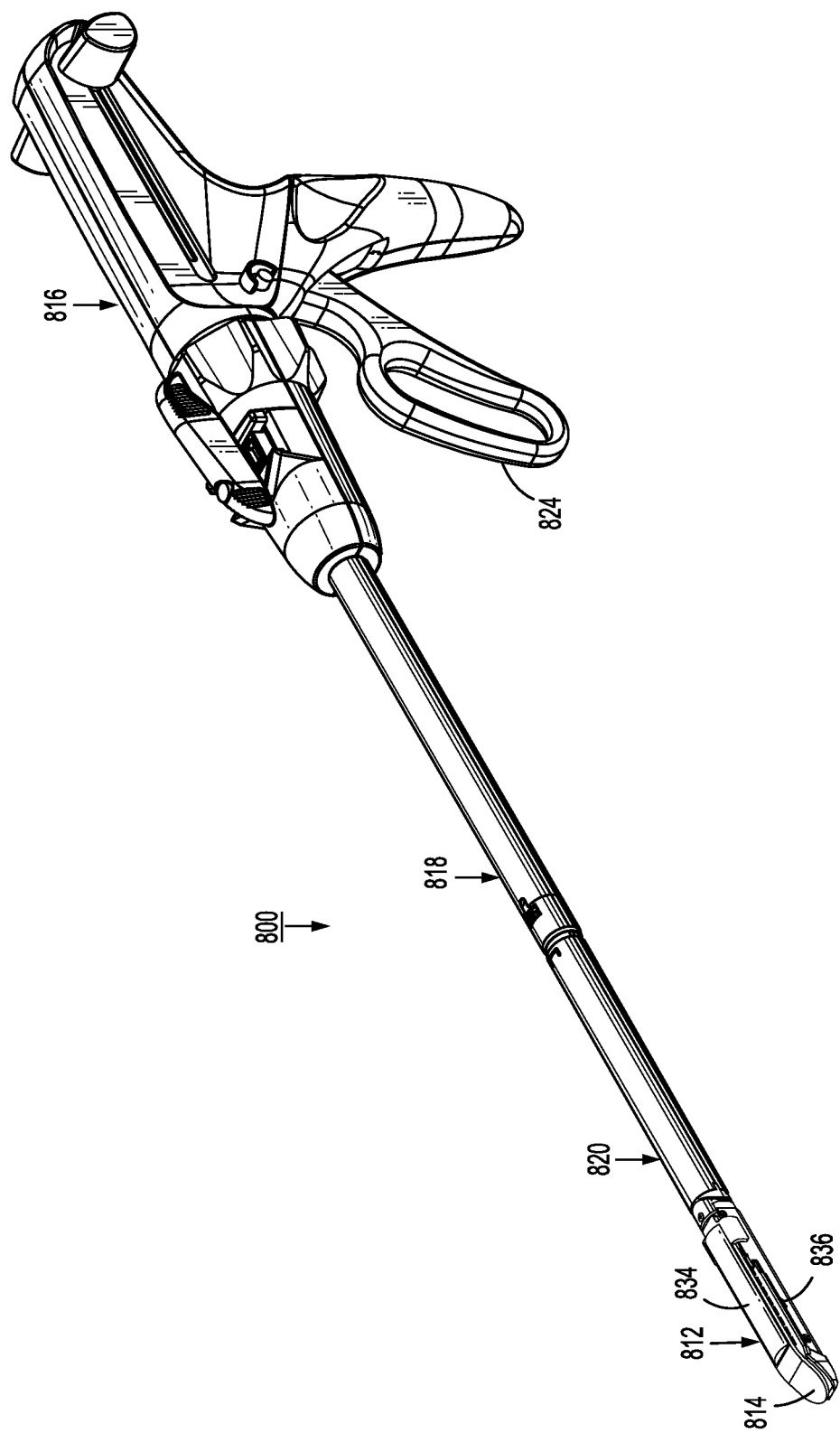
FIG. 13 is a side perspective view from above a surgical stapling device including another embodiment of the presently disclosed dissecting tip attached to the end effector thereof with the anvil assembly and cartridge assembly of the end effector in the open position.
Figure 13A:
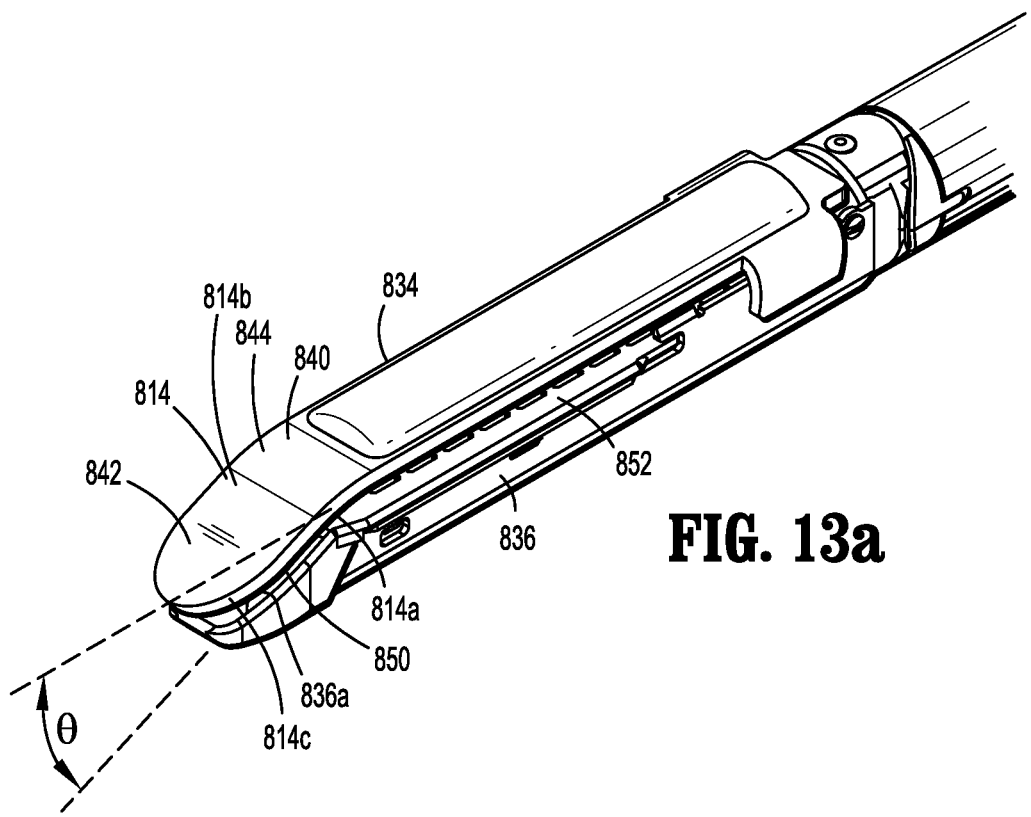
FIG. 13a is an enlarged side perspective view from above of the end effector of the surgical stapling device shown in FIG. 1 with the anvil assembly and cartridge assembly in the clamped position.
Figure 13B:
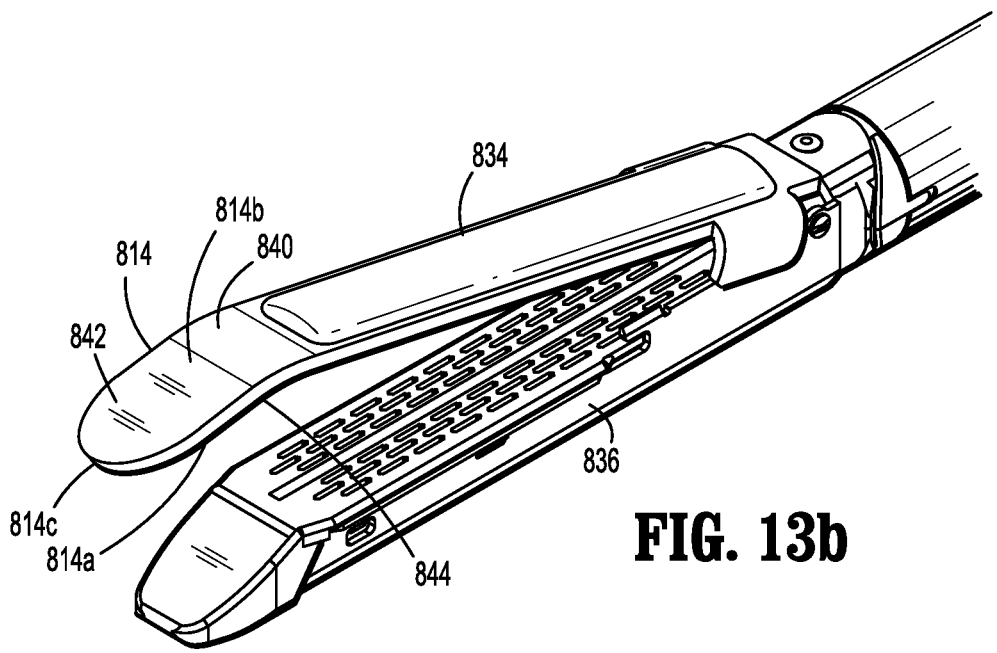
FIG. 13b is an enlarged side perspective view from above of the end effector of the surgical stapling device shown in FIG. 1 with the anvil assembly and cartridge assembly in the open position.
Figure 13C:
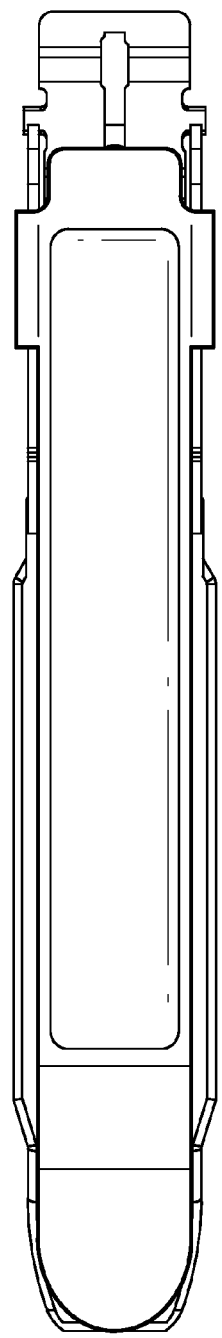
Figure 13D:
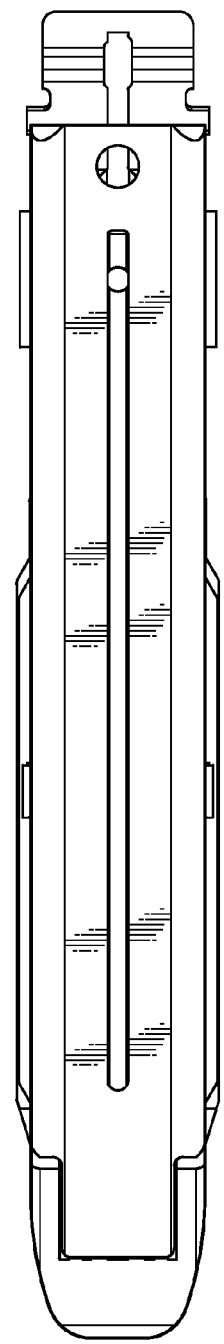
Figure 13F:
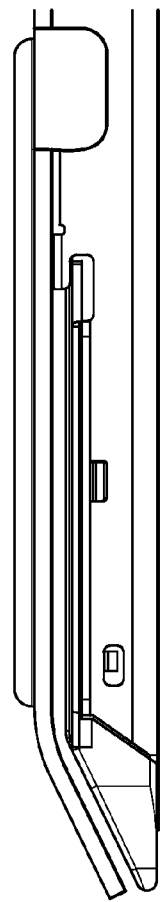
Figure 13E:
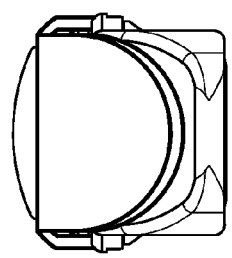
Figure 14A:
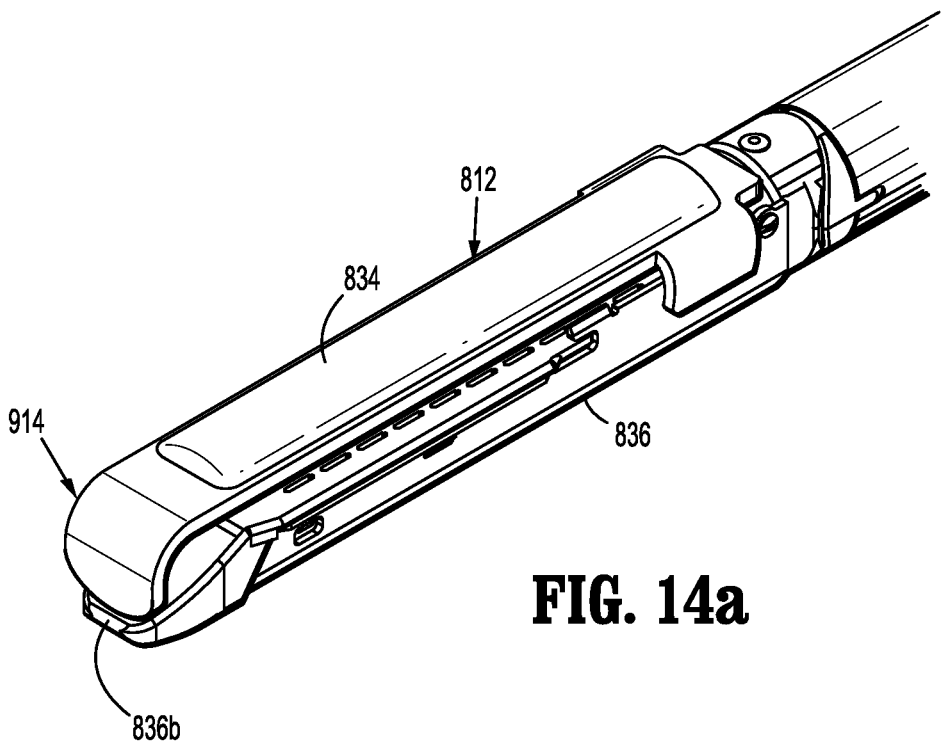
FIG. 14a is an enlarged side perspective view from above of another embodiment of the presently disclosed dissecting tip attached to an end effector with the anvil assembly and cartridge assembly of the end effector in the clamped position.
Figure 14B:
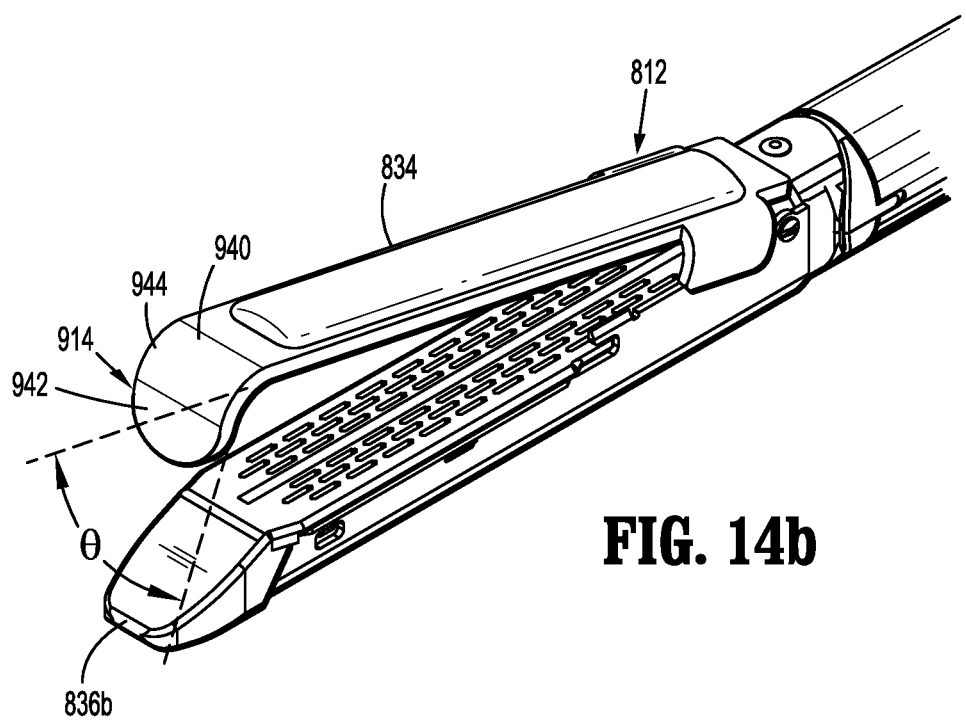
FIG. 14b is an enlarged side perspective view from above of another embodiment of the presently disclosed dissecting tip attached to an end effector with the anvil assembly and cartridge assembly of the end effector in the open position.
Figure 14C:
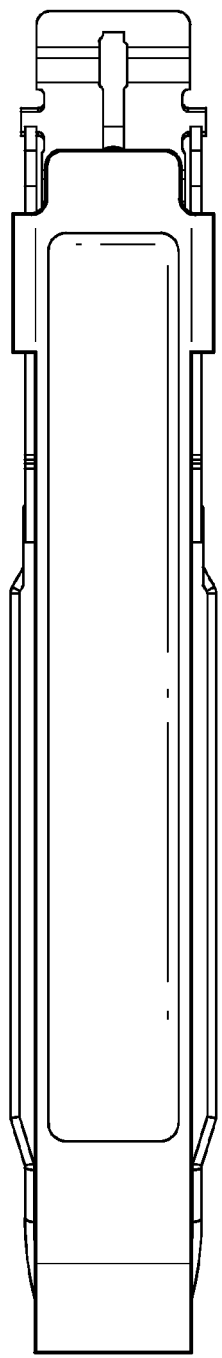
Figure 14D:
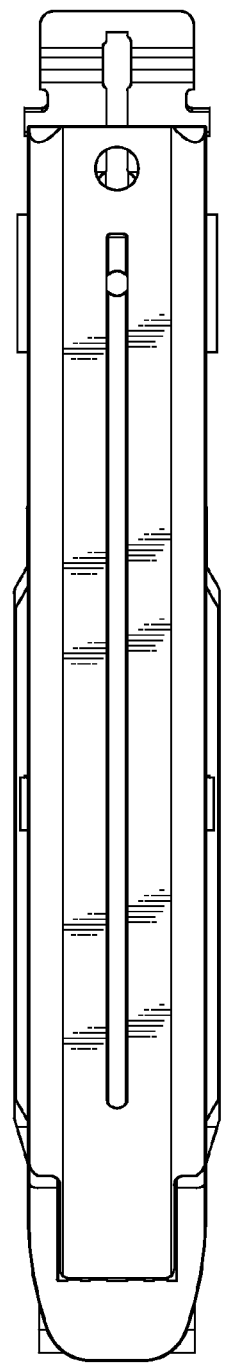
Figure 14F:
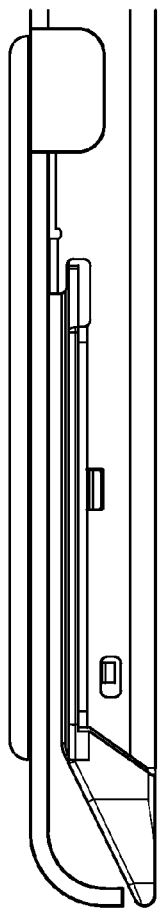
Figure 14E:
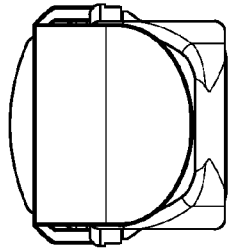

FIG. 13 illustrates a linear surgical stapling device known generally as 800 including an end effector 812 having another embodiment of the presently disclosed dissecting tip here designated 814, supported thereon. Stapling device 800 is substantially similar to stapling device 10 and includes a handle assembly 816 and an endoscopic portion 818. End effector 812 may form part of a disposable loading unit or single use loading unit (SULU) 820.

Referring to FIGS. 13a-13f, end effector 812 includes an anvil assembly 834 and a cartridge assembly 836 movably positioned in relation to each other between an open position (FIG. 13b) and a clamped or approximated position (13a). In one embodiment, anvil assembly 834 is pivotal in relation to cartridge assembly 836. Trigger 824 is movable through an actuation stroke or strokes to move anvil assembly 834 and cartridge assembly 836 between the open and closed positions as is well known in the art.

Referring to FIGS. 13a-13f, dissecting tip 814 extends distally from end effector 812. In this embodiment, dissecting tip 814 and anvil assembly 834 are of monolithic construction. Alternately, it is envisioned that dissecting tip 814 may be formed separately from anvil assembly 834 and secured thereto using any known fastening technique, e.g., adhesives, welding, soldering, brazing, pins, interlocking structure, etc. It is contemplated that dissecting tip 814 can be supported on another portion of end effector 812 such as cartridge assembly 836. Dissecting tip 814 may be formed from a surgical grade metal or plastic. It is also contemplated, however, that other known surgically approved materials may be used to construct dissecting tip 814.

Dissecting tip 814 includes a proximal portion 840 and a distal portion 842. Proximal portion 840 extends distally from anvil assembly 834 and includes a curved section 844. Curved section 844 defines a smooth transition between anvil assembly 834 and distal portion 842 of dissecting tip 814. The longitudinal axis of anvil assembly 834 and the longitudinal axis of distal portion 842 of dissecting tip 814 intersect to define an angle θ (FIG. 13a) of between about 5° and about 90°. In this embodiment angle θ is about 30°.

Distal portion 842 includes a semi-circular smooth distal face 814c. Proximal portion 840 and distal portion 842, together, define a smooth substantially flat inner surface 814a and a smooth substantially flat outer surface 814b. As illustrated, the width of dissecting tip 814 proximal of distal face 814c is substantially constant along the length of dissecting tip 814 and is about equal to the width of cartridge assembly 836. It is contemplated, however, that the width of dissecting tip 814 may vary along the length of dissecting tip, e.g., the width of dissecting tip 814 may be decreased or increased along the length of dissecting tip 814 from the proximal end of dissecting tip 814 to the distal end of the dissecting tip 814 or at any point therebetween. In this embodiment, the width of dissecting tip 814 does not exceed the width of cartridge assembly 836.

As illustrated in FIGS. 13a and 13c-13f, when anvil assembly 834 and cartridge assembly 836 are in their clamped position, a gap 850 is defined between a distal angled guide surface 836a of cartridge assembly 836 and inner surface 814a of dissecting tip 814. In this embodiment, gap 850 is substantially equal to or greater that gap 852 defined between the anvil and cartridge assemblies. It is envisioned that in some circumstances it may be desirable to reduce the height of gap 850 to a height smaller than gap 852, e.g., when it is desirable to clamp or compress tissue between guide surface 836a of cartridge assembly 836 and inner surface 814a of dissecting tip 814.

FIGS. 14a-14f illustrate another embodiment of the presently disclosed dissecting tip shown generally as 914. Dissecting tip 914 extends distally from end effector 812. In one embodiment, dissecting tip 914 is formed monolithically with anvil assembly 834 of end effector 812. Alternately, it is envisioned that dissecting tip 914 may be formed separately from anvil assembly 834 and secured thereto using any known fastening technique as set forth above. It is also envisioned that dissecting tip 914 can be supported by another portion of end effector 812 such as cartridge assembly 836. Dissecting tip 914 may be formed from surgical grade metals or plastics having the requisite strength requirements or any other known material suitable for surgical use.

Dissecting tip 914 is substantially similar in shape to dissecting tip 814 with the exception that angle θ is about 90°. More specifically, dissecting tip 914 includes a proximal portion 940 and a distal portion 942. Proximal portion extends distally from anvil assembly 834 and includes a curved section 944 which defines a smooth transition between anvil assembly 834 and distal portion 942 of dissecting tip 914. The longitudinal axis of anvil assembly 834 and the longitudinal axis of distal portion 942 of dissecting tip 914 define an angle θ of between about 80° and about 90°.

Figure 15:
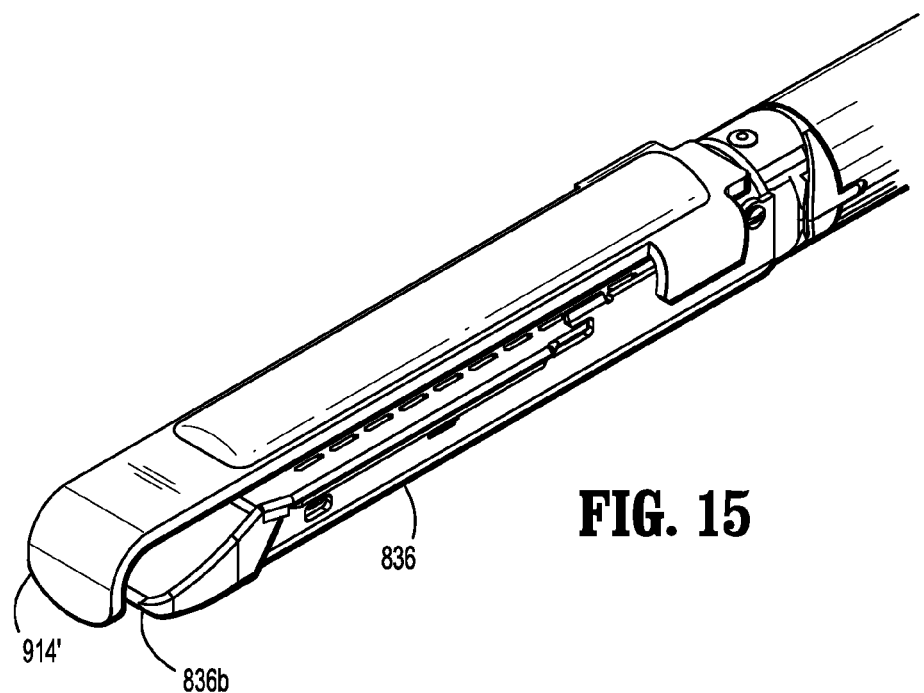
FIG. 15 is a side perspective view from above of another embodiment of the presently disclosed dissecting tip attached to an end effector with the anvil assembly and cartridge assembly of the end effector in the open position.
Figure 15A:
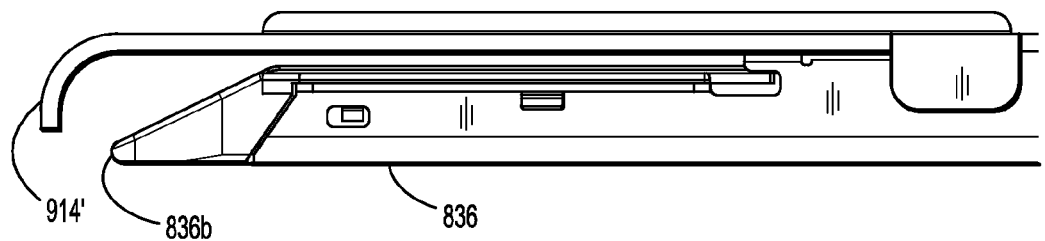
FIG. 15a is a side view of the end effector and dissecting tip shown in FIG. 15.

Distal portion 942 is similar in shape to that of distal portion 842 of dissecting tip 814 and will not be discussed in further detail herein. In one embodiment (See FIGS. 14a-14f), distal portion 942 of dissecting tip 914 extends distally to about or adjacent the distal end 836b of cartridge assembly 836 of end effector 812. In another embodiment (See FIGS. 15 and 15a), dissecting tip 914' is positioned distally of the distal end 836b of cartridge assembly 836 of end effector 812. In this embodiment, dissecting tip 914' is positioned to dissect tissue when the anvil and cartridge assemblies are in their clamped position.

Figure 16A:
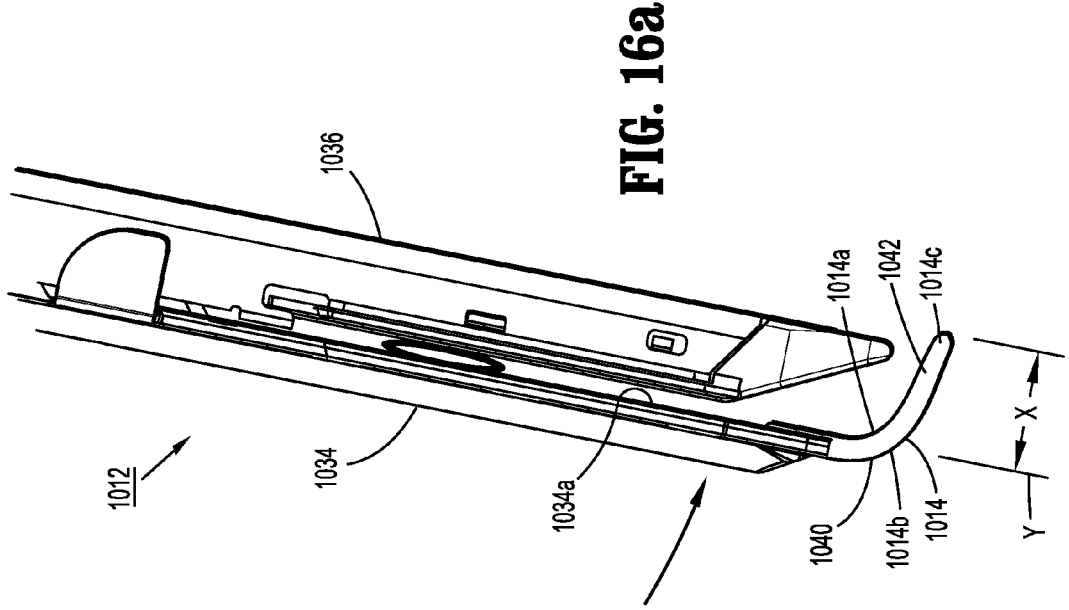
FIG. 16a is a side view of the end effector and dissecting tip shown in FIG. 16 with the anvil assembly and cartridge assembly of the end effector in the clamped position.
Figure 16:
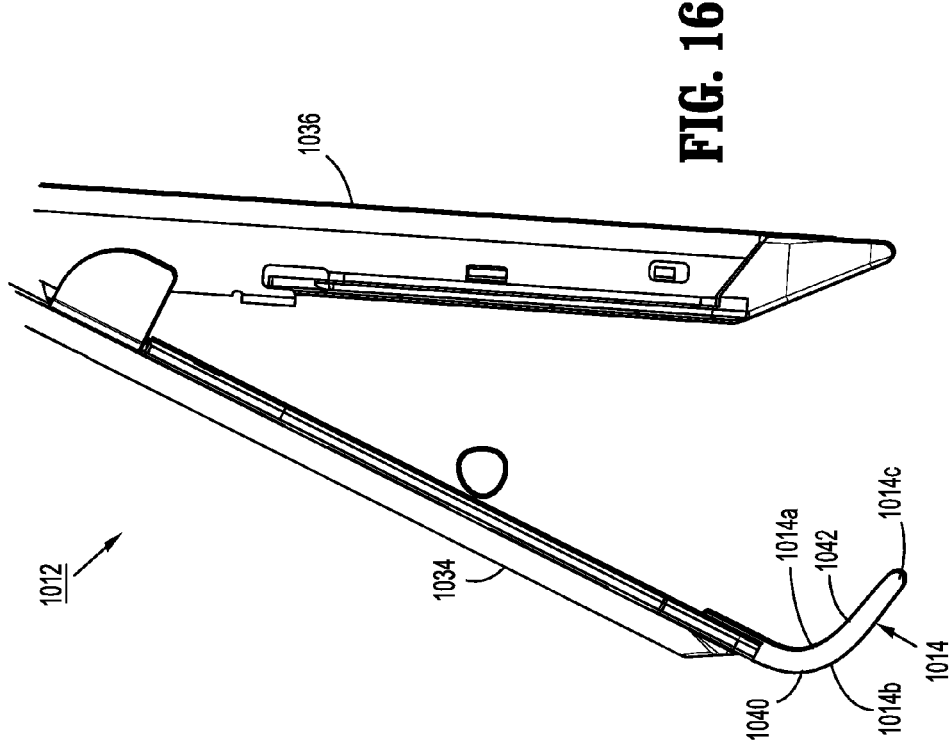
FIG. 16 is a side view of another embodiment of the presently disclosed dissecting tip attached to an end effector of a surgical instrument with the anvil assembly and the cartridge assembly of the end effector in an open position.
Figure 16B:
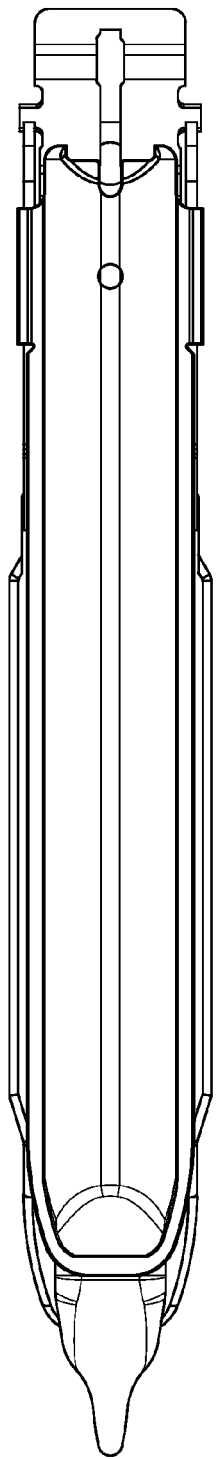
Figure 16C:
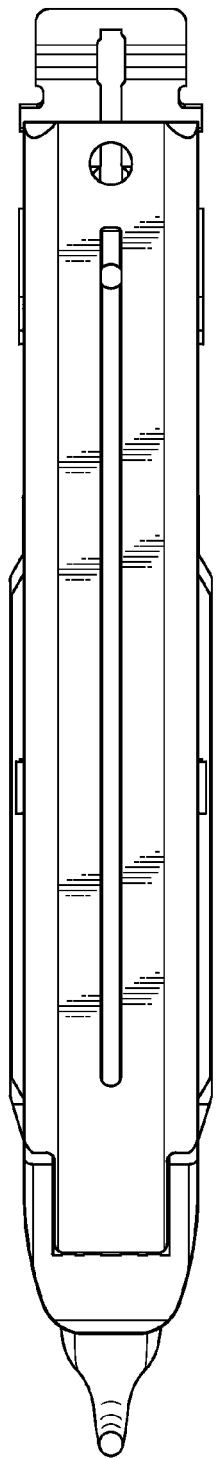
Figure 16E:
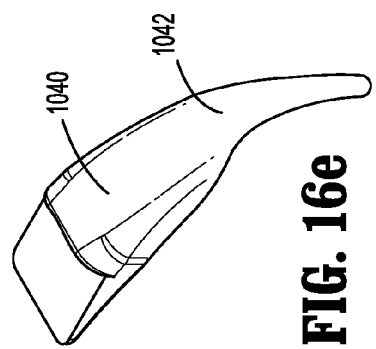

FIGS. 16-16e illustrate another embodiment of the presently disclosed dissecting tip shown generally as 1014. Dissecting tip 1014 is secured to the distal end of anvil assembly 1034 of end effector 1012 using any known suitable fastening technique, e.g., adhesives, welding, soldering, brazing, pins, etc. It is also envisioned that dissecting tip 1014 may be secured to end effector 1012 at other locations such as to cartridge assembly 1036. Alternately, dissecting tip 1014 may be formed monolithically or integrally with a portion of end effector 1012. Dissecting tip 1014 may be constructed from a surgical grade metal or plastic, although it is contemplated that other surgically approved materials may be used.

Figure 16D:
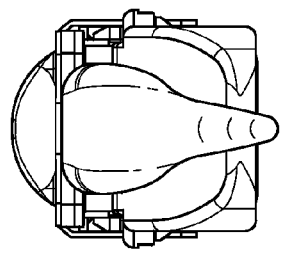

Dissecting tip 1014 includes a proximal portion 1040 and a distal portion 1042. Proximal and distal portions 1040 and 1042, respectively, are contiguous and define a curved inner surface 1014a, a curved outer surface 1014b and a distal tip 1014c. Distal tip 1014c is located on the distal end of distal portion 1042. In one embodiment, surfaces 1014a and 1014b are smooth to prevent dissecting tip 1014 from snagging, pulling and/or cutting tissue. In one embodiment, the width of distal portion 1042 of dissecting tip 1014 decreases substantially continuously from its proximal end to its distal end and culminates at distal tip 1014c which may be thin and blunt (See FIGS. 16d and 16e). It is also contemplated, however, that the width of the distal portion and/or proximal portion of dissecting tip 1014 may remain constant along its length or have a width which increases or decreases along any portion or all of its length. The width of dissecting tip 1014 at its greatest should be less than the width of cartridge assembly 1036 to facilitate insertion of end effector 1012 through a trocar assembly during endoscopic procedures. Alternately, where dissecting tip 1014 is employed on open surgical instruments, it may be desirable to increase the width of dissector tip 1014 beyond that of cartridge assembly 1036.

In one embodiment, distal portion 1042 and tip 1014c of dissecting tip 1014 have substantially round cross-sections which may be substantially circular or oval. The diameter of the oval or circular cross-section may decrease from the proximal end of distal portion 1042 towards distal tip 1014c. In one embodiment, the diameter of distal tip 1014c is from about 2 mm to about 6 cm, in one embodiment from about 2 to about 4 mm or about 3 to about 4 mm. In another embodiment, distal tip 1014c has a diameter of from about 4 mm to about 6 mm and in one embodiment from about to about 6 mm. It is also contemplated that proximal portion 1040 may also have a round cross-section which may decrease in diameter along its length.

Curved inner and/or outer surfaces 1014a and 1014b, respectively may be formed having any suitable radius of curvature which may define an arc of between about 5° to about 90°. In one embodiment the arc defined by curved inner and outer surfaces 1014a and 1014b is between about 50° and 90°. In another embodiment the arc is between about 60° and about 80° and in another embodiment (FIG. 16) the arc is between about 80° and about 90°. It is also contemplated that curved inner and/or outer surfaces 1014a and 1014b may be formed having a plurality of different radii of curvature.

The distance "X" (FIG. 16a) between a horizontal plane "Y" defined by tissue contacting surface 1034a of anvil assembly 1034 and distal tip 1014c may be between about 10 mm and about 30 mm. In one embodiment, the distance X is between about 25 mm and about 30 mm. It is noted that distance X may vary greatly depending on the type of instrument dissecting tip 1014 is employed on, e.g., open or endoscopic, and on the particular procedure the instrument is being employed to perform. Accordingly, a wide size range of dissecting tips is envisioned.

Figure 17A:
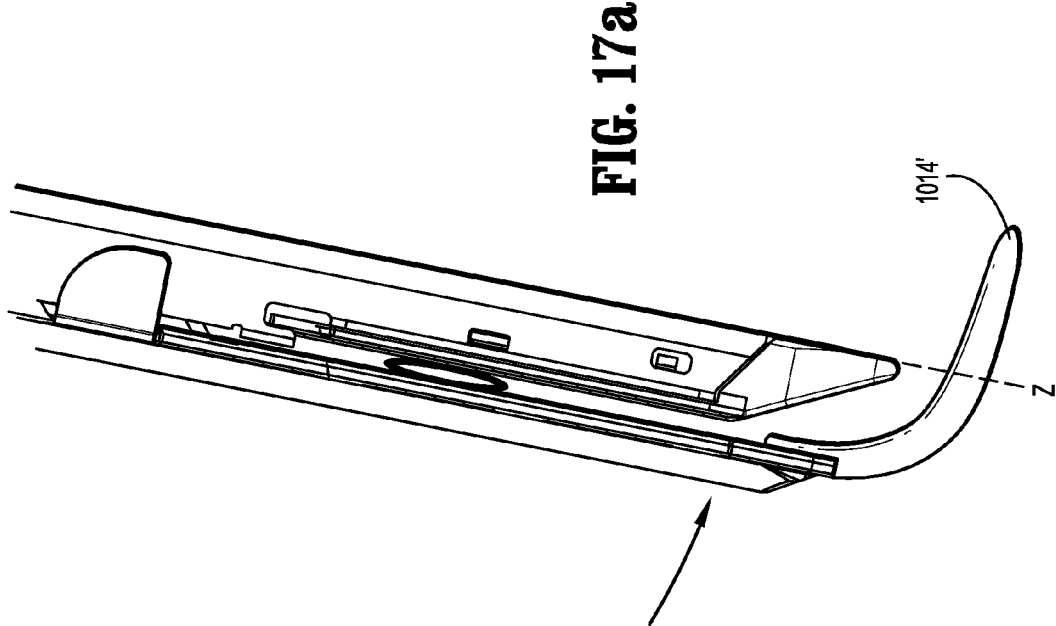
FIG. 17a is a side view of the end effector and dissecting tip shown in FIG. 17 with the anvil assembly and cartridge assembly of the end effector in the clamped position.
Figure 17:
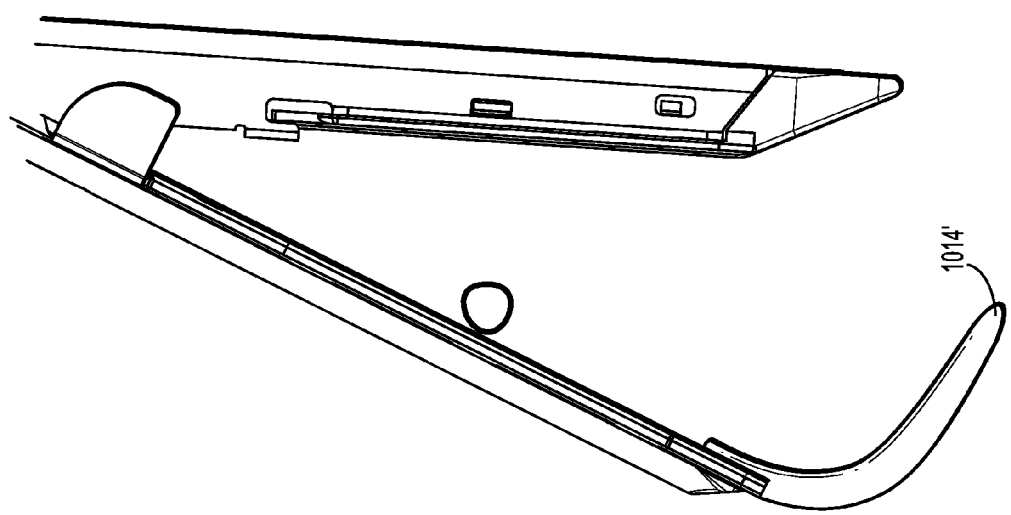
FIG. 17 is a side view of another embodiment of the presently disclosed dissecting tip attached to an end effector of a surgical instrument with the anvil assembly and the cartridge assembly of the end effector in an open position.
Figure 17B:
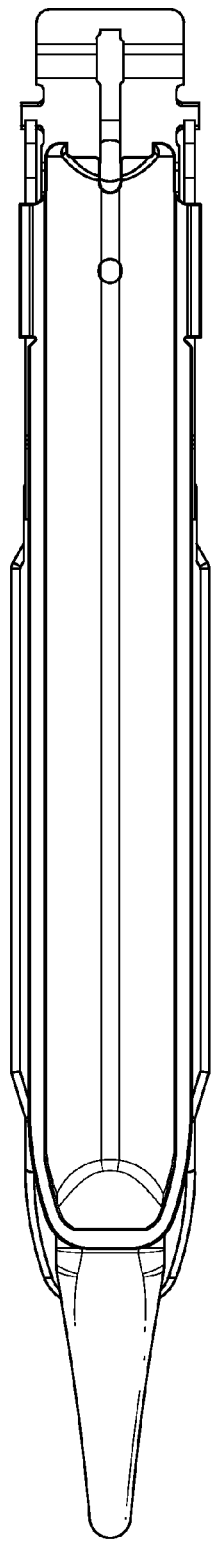
Figure 17C:
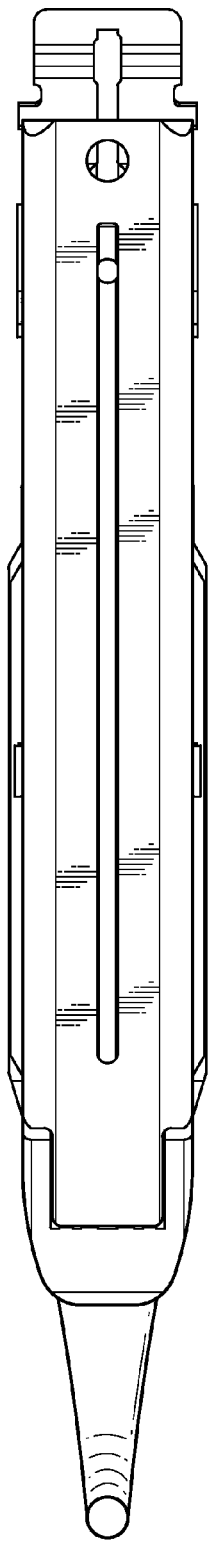
Figure 17E:
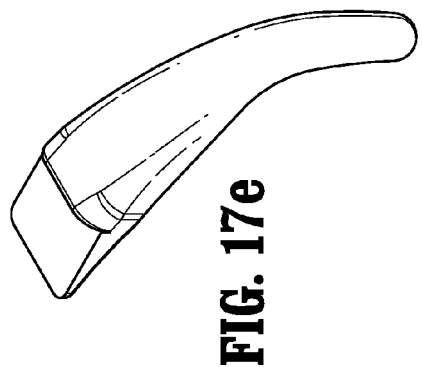
Figure 17D:
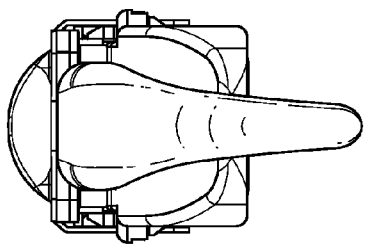

In one embodiment (FIGS. 17 and 17a), distal tip 1014' extends below a plane "Z" defined by the bottom surface of cartridge assembly 1036. By extending dissecting tip 1014' below the plane defined by cartridge assembly 1036, access to adherent tissue may be improved and visualization of dissecting tip 1014' is permitted. Visualization of dissecting tip 1014' facilitates confirmation that the dissecting tip is properly positioned and that dissection of adherent tissue is completed. This embodiment may be more suitable for use on instruments designed for open surgical procedures since an enlarged trocar would be required to facilitate passage of dissecting tip 1014'.

It will be understood that various modifications may be made to the embodiments disclosed herein. For example, the dissecting tip may be secured to other parts of the end effector including the cartridge assembly. Further, each of the dissecting tips may be monolithically or integrally formed with the end effector, e.g., anvil assembly or cartridge assembly. Moreover, the angles and/or curves of the dissecting tip surface(s) may be modified to better suit a particular surgical procedure. Therefore, the above description should not be construed as limiting, but merely as exemplifications of preferred embodiments. Those skilled in the art will envision other modifications within the scope and spirit of the claims appended hereto.

It is also envisioned that any of the dissecting tips described above may be incorporated into other surgical instruments which may require some tissue dissection prior to use. These instruments include surgical clip appliers and other ligation devices.

What is claimed is:

1. A method of performing a surgical procedure comprising:
positioning an end effector having an anvil assembly and a cartridge assembly adjacent target tissue when the anvil assembly and the cartridge assembly are in a clamped position;
pressing a dissecting tip of the end effector against the target tissue while maintaining the end effector in the clamped position to separate the target tissue from surrounding tissue, wherein the dissecting tip extends distally from one of the anvil assembly or the cartridge assembly and includes a tip end, the tip end being longitudinally and distally spaced a fixed distance from a distal-most end of the other of the cartridge assembly or the anvil assembly to engage the target tissue when the end effector is in the clamped position, the dissecting tip extending across a plane defined by a tissue contacting surface of the other of the cartridge assembly or the anvil assembly when the end effector is in the clamped position;
moving the end effector to an open position;
positioning the target tissue between the tissue contacting surface of the cartridge assembly and the tissue contacting surface of the anvil assembly; and
clamping the target tissue between the tissue contacting surface of the anvil assembly and the tissue contacting surface of the cartridge assembly.

2. The method of claim 1, wherein positioning the end effector includes inserting the end effector through a trocar cannula assembly.

3. The method of claim 1, wherein clamping tissue between the anvil assembly and the cartridge assembly includes moving the end effector to an open position, positioning the tissue between the anvil assembly and the cartridge assembly, and returning the end effector to the clamped position.

4. The method of claim 1, further including stapling the target tissue.

5. The method of claim 4, wherein stapling the tissue includes actuating a handle assembly of a stapling device supporting the end effector.

6. The method of claim 4, further including cutting the target tissue.

7. The method of claim 1, further including supporting the dissecting tip to one of the cartridge assembly and the anvil assembly.

8. The method of claim 1, wherein positioning the end effector includes articulating the end effector relative to an elongate body of a stapling device supporting the end effector.

9. The method of claim 1, wherein positioning the end effector includes rotating the end effector relative to a handle assembly of a stapling device supporting the end effector.

10. The method of claim 1, further including attaching the end effector to a handle assembly of a stapling device.

11. The method of claim 1, wherein the dissecting tip extends beyond the cartridge assembly when the end effector is in the clamped position.

12. The method of claim 1, wherein the dissecting tip is curved.

13. The method of claim 1, wherein pressing the dissecting tip of the end effector against the target tissue includes engaging a distal facing surface of the dissecting tip with the target tissue.

14. The method of claim 1, wherein pressing the dissecting tip of the end effector against target tissue includes engaging a proximal facing surface of the dissecting tip with the surrounding tissue.

15. The method of claim 1, wherein the dissecting tip is spaced from the cartridge assembly when the end effector is in the clamped position.

16. The method of claim 1, wherein the dissecting tip does not extend beyond a width of the end effector when the end effector is in the clamped position.

17. The method of claim 1, wherein the dissecting tip does not extend beyond a height of the end effector when the end effector is in the clamped position.

18. The method of claim 1, wherein the cartridge assembly supports a plurality of staples.

19. The method of claim 1, wherein the dissecting tip is fixedly secured to one of the anvil assembly and the cartridge assembly.

20. The method of claim 1, wherein the tissue contacting surfaces of the anvil assembly and the cartridge assembly are adjacent one another when the end effector is in the clamped position.

21. A method of performing a surgical procedure comprising:
   positioning an end effector having an anvil assembly and a cartridge assembly adjacent target tissue when the anvil assembly and the cartridge assembly are in a clamped position, each of the anvil assembly and the cartridge assembly defining a tissue contacting surface, the tissue contacting surfaces being in juxtapose relation when the anvil assembly and the cartridge assembly are in the clamped position;
   pressing a dissecting tip of the end effector against the target tissue while maintaining the end effector in the clamped position to separate the target tissue from surrounding tissue, wherein the dissecting tip extends distally from one of the anvil assembly or the cartridge assembly and includes a tip end, the tip end being longitudinally and distally spaced a fixed distance from a distal-most end of the other of the cartridge assembly or the anvil assembly to engage the target tissue when the end effector is in the clamped position, the dissecting tip extending through a plane defined by the tissue contacting surface of the other of the cartridge assembly or the anvil assembly when the end effector is in the clamped position;
   moving the end effector to an open position;
   positioning the target tissue between the tissue contacting surface of the cartridge assembly and the tissue contacting surface of the anvil assembly; and
   clamping the target tissue between the tissue contacting surface of the anvil assembly and the tissue contacting surface of the cartridge assembly.

22. The method of claim 1, wherein the tissue contacting surface of the cartridge assembly defines openings for receiving staples therethrough and the tissue contacting surface of the anvil assembly defines anvil forming pockets corresponding to the openings in the cartridge assembly.

23. The method of claim 21, wherein the tissue contacting surface of the cartridge assembly defines openings for receiving staples therethrough and the tissue contacting surface of the anvil assembly defines anvil forming pockets corresponding to the openings in the cartridge assembly.

* * * * *